United States Patent

Hirai

[19]

[11] Patent Number: 6,001,334
[45] Date of Patent: Dec. 14, 1999

[54] EXTREMELY HIGH DENSITY BARIUM SUSPENSION AS A CONTRAST MEDIUM FOR UPPER GASTROINTESTINAL EXAMINATION

[75] Inventor: Kazuzo Hirai, Kyoto-fu, Japan

[73] Assignee: Fushimi Pharmaceutical Co., Ltd., Kagawa-ken, Japan

[21] Appl. No.: 08/760,501

[22] Filed: Dec. 5, 1996

[30] Foreign Application Priority Data

Dec. 8, 1995 [JP] Japan ................................ 7-345032

[51] Int. Cl.⁶ .................................................. A61K 49/04
[52] U.S. Cl. ..................................................... 424/9.411
[58] Field of Search ........................................ 424/9.411

[56] References Cited

U.S. PATENT DOCUMENTS

| | | | |
|---|---|---|---|
| 3,216,900 | 11/1965 | Embring et al. | 167/95 |
| 3,539,682 | 11/1970 | Eriksson et al. | 424/4 |
| 5,160,724 | 11/1992 | Tonariya et al. | 424/4 |
| 5,405,600 | 4/1995 | Illig et al. | 424/5 |
| 5,525,327 | 6/1996 | Baker et al. | 424/9.45 |
| 5,543,132 | 8/1996 | Baker et al. | 424/9.411 |

FOREIGN PATENT DOCUMENTS 60-54919  3/1985  Japan .
60-61537  4/1985  Japan .

*Primary Examiner*—Gary E. Hollinden
*Attorney, Agent, or Firm*—Ostrolenk, Faber, Gerb & Soffen, LLP

[57] ABSTRACT

To provide a barium powder preparation and application thereof to an extremely high density barium suspension, processes for producing them, and a method of upper gastrointestinal examination, wherein double contrast radiography can be carried out on-the-fly without the use of a gastric tube and the injection of any parasympathicolytic, only by one slow rolling operation with the patient on the table. A barium powder preparation obtained by mixing specified proportions of large, medium and small component particles which are produced from large, medium and small particles of pure barium sulfate having specific particle properties, by adding Gum Tragacanth and Carrageenan in specified amounts and at a specified ratio, kneading their mixture under specified kneading conditions to fragment the molecules of Gum Tragacanth and Carrageenan and coat the particles with them, and drying and sterilizing the particles, and a barium suspension prepared by suspending the above barium powder preparation in water at an extremely high density are used.

6 Claims, 10 Drawing Sheets

Particle Size Distribution and Specific Surface Areas of the Small, Medium and Large Particles Particle Size Distribution and Specific Surface Areas of the Small, Medium and Large Particles

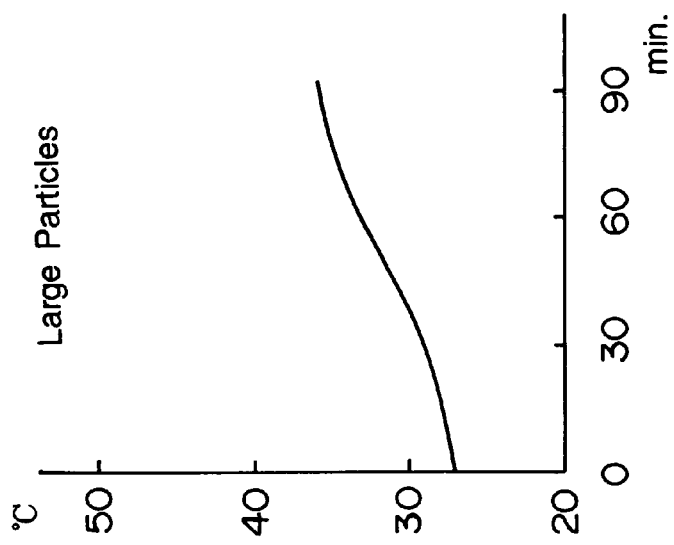
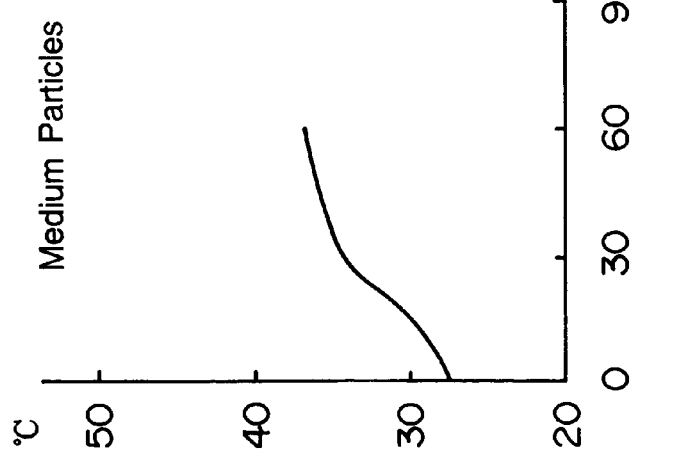
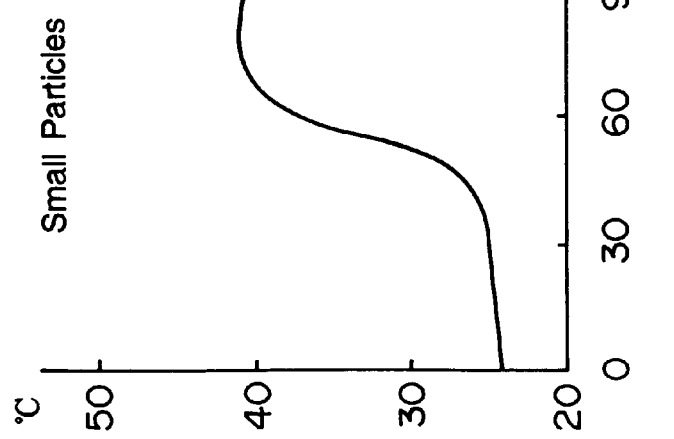

α: twisting angle
h: height of the bob (50 mm)
Ri: radius of the bob (7.2 mm)
Re: radius of the cup (8.15 mm)

R: radius of the cone (cm)
θ: conic angle of the cone (rad) = 4° (constant)
k: torsional constant of the wire (dyne·cm/rad)

Non-Newtonian Fluid (a): non-Newtonian flow (ideal)

(a'): pseudoplastic flow (b): plastic flow (c): dilatant flow $Y_0$: yield value $\eta_{ap}$: apparent viscosity

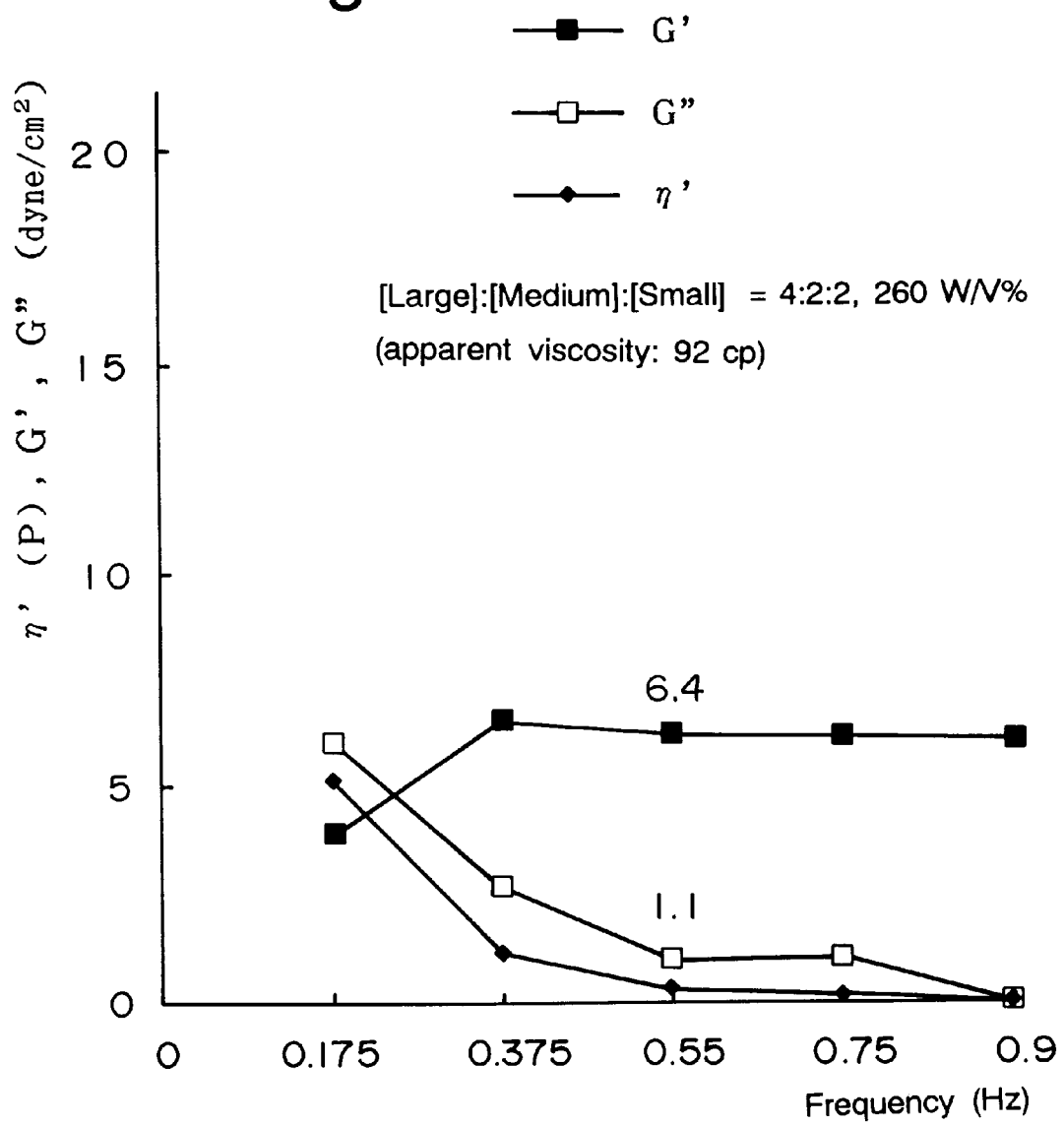

Sweeping by Extremely High Density Barium
(direction of "→" mark)

A Preferable State of Adhesion to Gastric Mucosa after Sweeping

Visualization of area gastricae at 260 W/V%

Total: 456 cases

6,001,334

EXTREMELY HIGH DENSITY BARIUM SUSPENSION AS A CONTRAST MEDIUM FOR UPPER GASTROINTESTINAL EXAMINATION

BACKGROUND OF THE INVENTION

1. Field of the Invention

The present invention relates to a novel barium powder preparation and application thereof to an extremely high density barium suspension used mainly for upper gastrointestinal double contrast examination, processes for producing them, and a method of X-ray examination applicable mainly to the diagnosis of early gastric cancer and peptic ulcer using said extremely high density barium suspension as a contrast medium.

2. Background Art

The X-ray examination of the stomach, duodenum and esophagus, especially for the double contrast method, requires highly skilled operation using gastric tubes, due to the fuzziness of the barium sulfate suspension (referred to simply as "barium" hereafter) used as a contrast medium, or its excessive or insufficient adhesion to the gastric mucosa, as is often the case. Improvement has long been awaited, as no ideal barium is commercially available yet. Although new products claiming "high density" have been released for the last few years, their densities in practical use are only about 200 W/V%, and fall short of addressing the aforementioned problems.

The environment surrounded by gastric mucosa is unique and severe, containing free acids and some mucus in an ordinary way. The mucosal surface is covered with the protecting layers of mucus, such as Mackintosh's barrier mucus and Katsuyama's surface mucous gel layer (SMGL), and not easily accessible. Even a time-tested barium with a density of 140 W/V% (Baritogen DX, tradename of Fushimi Seiyakusho Co. Ltd.) would require, for a double contrast examination, a number of rigorous body rolling operations to wash out the mucous layers, in addition to the use of a gastric tube to remove the free gastric mucus, to obtain a preferable result.

Body rolling is an operation to change the patient's posture by turning the patient's body on a horizontal table by 90° alternately to the bilateral sides from the supine position. If the amount of mucus is large, it needs to be sucked out through a gastric tube. However, it is practically not easy to suck out dense gastric mucus. For example, the insertion and removal of a gastric tube may be difficult in some patients. Also, inserting a gastric tube may induce unexpected secretion of gastric juice or peristalsis, bringing about an adverse effect. Furthermore, the double contrast examination requires time-consuming air injection through a gastric tube while monitoring the amount of injection using a large cylinder. Therefore, a significant amount of parasympathicolytic usually needs to be administered in advance to suppress the peristalsis and mucous secretion during the injection intramuscularly and, at times, both intramuscularly and intravenously. These complicated procedures make most non-specialists hesitant to use this examination method.

There is a huge amount of literature, including books and journals, on the detailed procedures available in Japan. For example, the rolling method for double contrast radiography has been frequently described with diagrams called "Stomap" and detailed explanation, such as the position, direction and angle of posture change.

Weirdly, however, no clear description has been provided on the speed of rolling. Instructions previously given require to roll as quickly as possible, rock or wash, or swing the hips as an Hawaiian dance. These seemingly descriptive but quite vague expressions may not help a lot in practice.

As mentioned above, the double contrast radiography of the stomach depends largely on the skills of the operator, due to the complexity of the conditions such as the complicated environment of the gastric mucosa, difference in barium density, visco-elasticity of individual contrast medium, and rolling method. From the viewpoint of rolling mechanics in double contrast examination, a barium density of 140 W/V% or less requires quick and repeated rolling until the barium forms a desired thin layer over the gastric mucosa in order to remove the mucus. However, excessive rolling may result in insufficient adhesion of the barium to the gastric mucosa, as the barium density may decrease due to dilution by the mucus.

The lately commercialized high-density agents with rated barium densities of 200 W/V% or over have a common disadvantage of easily precipitating and forming sludge. This overly high visco-elasticity hampers spreading of the medium and makes it a too thick layer and, therefore, visualizes only the gastric folds but not the gastricae area. A super-high density agent (tradename: EZ-HD) produced by an U.S. company with a barium density of 250 W/V% has the disadvantage of forming an excessively thick barium layer that cannot be reduced no matter how quick or repetitively rolling is done.

A high-density preparation of barium sulfate used as an X-ray double contrast medium is available from China (manufactured by National Chintao Tonfon Chemical Factory). The supplied technical document says it may be used for the X-ray double contrast examination of the esophagus and stomach. In use, 500 g of powder are mixed with an appropriate amount water and stirred for 5 minutes to make a suspension. It needs to be stirred again immediately before use for uniformity. Combination with an effervescent agent (Chintao No. 3) is recommended for a better result. In the supplied barium density dilution table, 39 ml of water is used to prepare a 300 g of 280 W/V% suspension with a total amount of 107 ml and a viscosity of about 300 mPa·s. Assuming 1 cp as 1 mPas·s, the viscosity is twice that of the applicant's extremely high density barium, which is 150 cp (see Table 7) at an equal density of 280 W/V%.

An analysis by the applicant revealed that the agent contains almost no small particles and is composed chiefly of large particles which have a specific surface area of 0.206 $m^2/g$ and a particle size distribution with a steep peak at 10 $\mu m$. Its scanning electron microscope image shows that it is made of crushed particles of natural barite. Unknown additives account for a mere 0.05%. The biggest problem is that, because it is made of crushed particles, the appearance is not clear white, unlike commonly available agents, posing a risk of contamination by foreign matter other than pure barium. A second problem is that it easily precipitates, as is the case for agents composed of large particles and no small particles. The large particles are similar to the large component particles of the present invention, but slightly larger. The rated density excludes the additives. As mentioned above, this barium sulfate has an apparent viscosity twice as high and no distinctive properties.

Also, another technology related to high-density barium has been proposed (Laid-open Japanese Patent Application No.60-54919, "A Process for Producing Barium Sulfate with Increased Fluidity and Density Suitable as a Contrast Ingredient in X-Ray Contrast Medium, Products Obtained by the Process, and an X-Ray Contrast Medium Produced Therefrom").

The technology can be summarized as follows: First, the pure barium (synthetic) used as a material is impregnated with ammonium sulfate and other salts, and sintered at a high temperature of 800 to 1200° C. This step removes the edges of the crystals to make their surface round and flat, allowing significantly efficient packing. The preferred particle size of the material is 1 to 5 μm. After the above step, a suspension of this powder, to which an appropriate amount (3%) of a few composite assistants have been added, has a density of 200 W/V% and a viscosity no more than 1000 mPas·s. Assuming 1 cp as 1 mPas·s, this barium sulfate has an extraordinarily high viscosity. The detailed description of the invention refers to barium sulfate agents obtained from crushed natural barite, or so-called crushed particles, and points out, by citing the argument by E. Miller, that "regrettably they generally do not meet the standard purity of the medical literature (Pharmacopoeia) as they contain excessive amounts of heavy metals."

Also, another technology related to high-density barium has been proposed (Laid-open Japanese Patent Application No.60-61537, "An X-Ray Contrast Medium").

This X-ray contrast medium is a powder agent having two peaks in the particle size distribution, one of which is in the large and the other of which in the small region, containing lignin sulfonic acid and alkali citrate as surfactants to decrease the viscosity and increase the stability of the barium suspension. Both of these two additives have been known to decrease viscosity (former in West German Patent No. 2028025, and latter in U.S. Pat. No. 3,216,900). However, the technology seeks a synergistic effect of using them together. For the particle size distribution with two peaks, Vol. 35, p.95, Journal of the Osaka Medical School, 1976, by the applicant is cited.

As a result, a viscosity of 60 sec (DAB8) was obtained at 2.5 g/ml (250 W/V%). Compared to the viscosity of 80 to 110 sec of the aforementioned Chinese barium sulfate at 250 W/V%, it is significantly low. However, no reference is made to the viscosity at an extremely high density of 260 W/V% or above, or to specific clinical performance.

SUMMARY OF THE INVENTION

An object of the present invention is to provide a novel barium powder preparation, an extremely high density barium suspension as a contrast medium for upper gastrointestinal examination, processes for producing them, and a novel method of upper gastrointestinal examination, wherein a procedure for washing the mucosal surface by repeated, furious and quick rolling as required for barium in the prior art is unnecessary; one slow rolling operation with a patient on the table is enough to easily visualize fine mucosal structures, including gastricae area, on a double contrast picture; in general, the use of a gastric tube is unnecessary; double contrast radiography can be carried out on-the-fly without the injection of a parasympathicolytic for suppressing mucous secretion and peristalsis; high contrast is achieved while fuzziness characteristic of high voltage radiography is minimized; gastric mucosa with a large amount of mucus can be swept by rolling at a low speed; only a small amount of contrast medium is required, serving for comfort and reducing side effects such as constipation, to make the examination procedure easier and relieve the physical stress on the patients, which makes the X-ray gastric examination useful for application to old, grave or handicapped patients, who have difficulty in changing postures; and the discovery of early gastric cancers and the upper gastrointestinal diagnosis of gastric ulcer and other diseases are enabled.

The inventor, after careful deliberation to solve the aforementioned problems, has completed the present invention according to the finding that they can be solved by means of a barium powder preparation obtained by mixing specified proportions of large, medium and small component particles of barium which are produced from large, medium and small particles of pure barium sulfate with a specific particle size distribution, by adding two kinds of additives, Gum Tragacanth and Carrageenan, which are natural macromolecular polysaccharides having long molecular chains, in specified amounts and at a specified ratio, kneading the mixture under specified kneading conditions to fragmentize the molecular chains of Gum Tragacanth and Carrageenan and coat the particles with them, and drying and sterilizing them; a barium suspension prepared by suspending said barium powder preparation in water at an extremely high density; and a new method of upper gastrointestinal examination using said barium suspension.

A first aspect of the present invention is a barium powder preparation consisting of large, medium and small component particles of pure barium sulfate coated with a composite additive consisting of Gum Tragacanth and Carrageenan, said large, medium and small component particles being mixed at a weight ratio of [large component particles]:[medium component particles]:[small component particles]=2:1:1, the particle size distribution of said original pure barium sulfate particles being normal distribution, as measured by a Coulter Counter, having peaks preferably at 8 μm for the large particles, 2.0 to 2.5 μm for the medium particles, and 0.8 to 1.0 μm for the small particles, the specific surface area ratio being [large component particles]:[medium component particles]:[small component particles]=1:2.8~3.3:6.9~7.5, the additional ratio of the contents of Gum Tragacanth and Carrageenan in said composite additive in each type of component particle being 1:10 for said large component particles, 1:9±1 for said medium component particles, and 1:0.9±0.1 for said small component particles, and the ratio of the effective Gum Tragacanth contents in said component large, medium and small particles is [large component particles]:[medium component particles]:[small component particles]=1:2.8~3.3:6.9~7.5, as is the specific surface area ratio, wherein said effective Gum Tragacanth contents are calculated using the following formula, Effective Gum Tragacanth content [Gum Tragacanth content]+ [Carrageenan content]×½.5, (wherein the contents is expressed in weight percent, and the viscosity reduction effect of Gum Tragacanth is assumed as 2.5 times that of Carrageenan).

The particle size distribution is measured by Coulter Counter as the number of particles passing through pores of three sizes (10, 30 and 100 μm), for 16 fragments ranging from 0.5 μm to 20.2 μm, using 3.2% NaCl solution with a measured internal resistance of 5 to 10 kΩ that has been filtrated through 0.2 μm filter paper as an electrolyte. The measurement is corrected for concurrent passing. The background (dust particles in a trace amount) in the above electrolyte which has been measured in advance is subtracted. Assuming all the particles as spherical, the surface area and volume of the particles in each fragment are calculated. The volume multiplied by the specific gravity of pure barium sulfate, 4.5, gives the weight. The sums of the surface area and weight of all the fragments give the total surface area and weight of all the particles that have passed through. The former divided by the latter gives the specific surface area in $m^2/g$. Medium particles that have passed through with a distribution peak at 2.52 μm have a total surface area of 1,373,206 μm and a total weight of 2,050,992.9 μg. Therefore, a specific surface area of 0.66953 $m^2/g$ is obtained by dividing the former with the latter.

Table 1 shows the result of measurement by a Coulter Counter, and how the particle size distribution and specific surface area of the medium particles are calculated.

provided to allow for the variation in the available material, not for the measurement error of the Coulter Counter. The preferable peak of the large particles is fixed at 8 μm, reflecting the fact that the large particles of pure barium sulfate used as the material have no variation. Therefore, the specific surface area calculated from the measured particle size distribution is also fixed with no allowance. This is also why the specific surface area of the large particles, which do not vary in particle size, is used as the reference in deter-

TABLE 1

Example of Measurement by Coulter Counter (Medium Particles)

| Particle size | Back ground | Concurrent passing | Number | Measurement | Concurrent passing | Number | | Frequency (%) | Weight per channel | Surface area per channel |
|---|---|---|---|---|---|---|---|---|---|---|
| 0.500 | | 1 | 0 | | 1 | 0 | | 0 | 0 | 0 |
| 0.630 | 2517 | 1.00 | 2522.43 | 34734 | 1.02977 | 33245.7 | | 0.9550008 | 19586.998 | 41454 |
| 0.794 | 853 | 1.00 | 853.624 | 41116 | 1.03524 | 41711.4 | | 2.3986298 | 49195.728 | 82612.5 |
| 1.00 | 196 | 1.00 | 196.033 | 43202 | 1.03703 | 44605.7 | | 5.1243385 | 105099.82 | 140133 |
| 1.26 | 63 | 1.00 | 63.0034 | 37813 | 1.03241 | 38975.6 | | 8.9567605 | 183702.52 | 194394 |
| 1.59 | 48 | 1.00 | 48.002 | 28768 | 1.02466 | 29429.4 | | 13.589994 | 278729.82 | 233736 |
| 2.00 | 10 | 1.00 | 10.0001 | 18830 | 1.01614 | 191239 | | 17.575747 | 360477.33 | 240318 |
| 2.52 | 5 | 1.00 | 5.00002 | 9837 | 1.00843 | 9914 | 94 | 18.227991 | 373854.81 | 197807 |
| 3.17 | 2 | 1.00 | 2 | 4310 | 1.00369 | 4323 | 92 | 15.823503 | 324538.94 | 136504 |
| 4.00 | 1 | 1 | 1 | 1455 | 1.00125 | 145581 | | 10.703677 | 219531.67 | 73177.2 |
| 5.04 | | 1 | 0 | 324 | 1.00028 | 324.09 | | 4.7665504 | 97761.611 | 25862.9 |
| 6.35 | | 1 | 0 | 40 | 1.00003 | 40.0014 | | 1.1766384 | 24132.771 | 5067.25 |
| 8.00 | | 1 | 0 | 7 | 1.00001 | 7.00004 | | 0.4117348 | 8444.6517 | 1407.44 |
| 10.8 | | 1 | 0 | 2 | 1 | 2 | | 0.2894336 | 5936.2631 | 732.872 |
| 12.7 | | 1 | 0 | | 1 | 0 | | 0 | 0 | 0 |
| 16.0 | | 1 | 0 | | 1 | 0 | | 0 | 0 | 0 |
| 20.2 | | 1 | 0 | | 1 | 0 | | 0 | 0 | 0 |
| TOTAL | | | 3701.09 | | | 223159 | | 100 | 2050992.9 | 1373206 |
| | | | | | | | | | Specific surface area | 0.66953 |

(Internal resistance: 10 kΩ, Electrolyte 3.2% NaCl)

FIG. 1 shows examples of the relations between the measured particle size distributions of the large, medium and small particles and their specific surface areas determined according to the measurement.

The barium powder preparation, as has often been pointed out, may have inferior visualization depending on production lots. The variation in the physical properties of the powder, such as viscosity, may cause excessive or insufficient adhesion to the gastric mucus or enhanced fuzziness. The chemical composition and purity of pure barium sulfate used as the material is strictly controlled by the Japanese Pharmacopoeia. However, physical properties such as particle size or viscosity are hardly controlled. As a result, variation in physical properties by lot remains unimproved. A solution has been awaited long by users. The inventor also had the problem of lot-by-lot variation in the particle size distribution of the medium and small particles in using pure barium sulfate as a material. Consequently, an additional measure was necessary to cope with the unfavorable effect on the four physical properties listed as below. An examination by the inventor has revealed an unavoidable difficulty that dividing barium sulfate powder ranging approximately from 0.8 μm to 20 μm into the three groups of large, medium and small particles having ideal particle size distributions was almost unpracticable.

In the particle size distribution of the large, medium and small particles of pure barium sulfate used as the material for the present invention, the preferable peaks of the medium and small particles are flexibly set in the ranges of 2.0 to 2.5 μm, and 0.8 to 1.0 μm, respectively. The flexibility is mining of the specific surface areas of the large, medium and small particles. The medium and small particles of pure barium sulfate used as the material, because of their variation as mentioned, have specific surface areas ranging from 2.8 to 3.3 times and 6.9 to 7.5 times, respectively, that of the large particles. These variations in particle size of the medium and small particles required the flexible setting of the effective Gum Tragacanth content in the composite additive.

Table 2 shows the viscosity reduction effects of the component particles at the contents determined according to the specific surface areas.

As the original large particles have a particle size distribution with its peak fixed at 8 μm, the specific surface area calculated from the measured particle size distribution is also fixed at one value of 0.23 $m^2/g$. In the medium particles, however, the peak is vague and almost flat, as shown in FIG. 1, and, as mentioned earlier, pure barium sulfate available as the material has varying peaks depending on the lot, ranging from a maximum of 2.5 to a minimum of 2.0 μm. Accordingly, the specific surface area calculated from the measured particle size distribution varies between 0.664 to 0.759 $m^2/g$. Therefore, its ratio to the specific surface area of the large particles, 0.23 $m^2/g$, also ranges from 1:2.8 to 1:3.3. The effective Gum Tragacanth content of the medium particles must fall in the range of 2.8 to 3.3 times that of the large component particles. Note that the content is not set arbitrarily in this range; it is determined according to the specific surface area calculated using the measured particle size distribution of the medium particles. In other words, the particle size distribution should be measured for individual material lots and specific surface area be calculated according to its variation, to select the appropriate effective Gum Tragacanth content in the medium particles. The minimums and maximums of the specific surface area and the factor correspond to medium particles with the largest and smallest sizes, respectively. Thus, it is obvious that the specific surface area and ratio for a lot with an intermediate particle size take values in-between according to the measurement.

The small particles used as the material also have particle size variation, ranging from 1.0 $\mu$m to 0.8 $\mu$m in peak and 1.587 m$^2$/g to 1.725 m$^2$/g in specific surface area. Small particles available as material have a peak at the lowest 0.8 $\mu$m in most lots, and hardly at 1.0 $\mu$m. Therefore, practical inconvenience caused by fixing the particle size as in the large particles would not be serious. However, extra-small particles below 1.0 $\mu$m increase the apparent viscosity easily when suspended, and have a large specific surface area and inferior acid resistance. In order to increase the viscosity reduction effect, the Gum Tragacanth content needs to be raised, which, in turn, increases the dynamic modulus (G'), dynamic loss (G"), and yield value, resulting in excessive adhesion, agglutination with mucus, and fuzziness. On the other hand, small particles with a relatively large size of 1.0 $\mu$m are much more preferable than the extra-small ones, having a superior viscosity reduction effect when mixed with large and medium particles, while lowering the four viscometric coefficients, which are closely related to the visualization as will be explained later.

Thus, 1.0 $\mu$m is an ideal size for small particles, which is why the particle size is set flexibly to the range of 0.8 to 1.0 $\mu$m. Accordingly, the specific surface area is also set flexibly as above, as in the case of the medium particles, and so is the ratio of the effective Gum Tragacanth content, which ranges from 6.9 to 7.5 times that of the large particles. In a lot having an intermediate peak at, for example, 0.9 $\mu$m, the effective Gum Tragacanth content is to be selected, as explained for the medium particles, according to the specific surface area calculated using the measured particle size distribution.

The apparent viscosity is measured by a double rotating cylinder rheometer (Emila's rheometer) with a quadruple-speed rotor at a shear rate of 750 sec$^{-1}$ and a temperature of 24±1° C. Other properties are measured by a cone-plate type rheometer (Shimadzu rheometer Model RM-1) at a conic angle of 4°, a cone radius of 4 cm, a tip-to-plate gap of 175 $\mu$m, a torsional constant of wire of 2.205×106 (dyne·cm/rad), and a temperature of 24±1° C. For dynamic modulus measurement, higher-class rheometers are available, such as one from Carri-Med's CSL Rheometer (made in U.K.), which automatically control the stress using pneumatic bearings, instead of a spring. However, their conic angle is 1° and the cone-tip-to-plate gap is 55 $\mu$m. This narrow tip-to-plate gap is inadequate for measuring a barium suspension with coarse particles, particularly one with extremely high density. On the other hand, the gap in the Shimadzu model above may help reduce, especially in a dynamic measurement, the fluctuation in the vibration waveform caused by excessive approach during the measurement and the artificial suppression of amplitude due to overly stress control, thus reproducing the visco-elasticity waveform more precisely.

The values of G' and G" above are measurements at a plate moving frequency of 0.55 Hz.

All the four coefficients listed above are indicated as respective lower and upper limits in the density range of 260 to 290 W/V%. It is obvious, therefore, that the coefficients take intermediate values at an intermediate density like 270 W/V%, for example.

The maximum density of extremely high density barium is 290 W/V%. If the density exceeds the limit and reaches 300 W/V%, the apparent viscosity suddenly increases to 300 cp, G' to 97 dyne/cm$^2$, and G" to 87 dyne/cm$^2$, leaving only the yield value at a moderate 12 dyne/cm$^2$ and making it unusable as a contrast medium. However, the extremely high density barium may be used as a contrast medium below the indicated minimum density of 260 W/V%. A preferable barium density is 270 W/V%, where the apparent viscosity is approximately 100 cp, yield value and G" are 6 dyne/cm$^2$ or less, low enough to show sufficient fluidity, and G' is

TABLE 2

Viscosity Reduction Effects of the Component Particles at the Contents Determined According to the Specific Surface Areas
(BaSO$_4$ powder: 50 g; water 17 ml; 176 ± 1 W/V %)

| Particle size | Particle size peak ($\mu$m) | Specific surface area and its ratio (m$^2$/g) | | Practical content T: Gum Tragacanth C: Carrageenan | Effective Gum Tragacanth content and its ratio | | Viscosity ($\eta_{ap}$) |
|---|---|---|---|---|---|---|---|
| Large | 8.0 | 0.23 | 1.0 | T 0.05% + C 0.15% | 0.075% | 1.0 | 16 |
| Medium | 2.0~2.5 | 0.644~0.759 | 2.8~3.3 | T 0.05% + C 0.4% ~ T 0.05% + C 0.5% | 0.21%~0.25% | 2.8~3.3 | 18 |
| Small | 0.8~1.0 | 1.587~1.725 | 6.9~7.5 | T 0.4% + C 0.3% ~ T 0.4% + C 0.4% | 0.52%~0.56% | 6.9~7.5 | 20 |

A second aspect of the present invention is an extremely high density barium suspension for upper gastrointestinal examination with a density of 260 to 290 W/V%, as expressed in pure barium sulfate weight/volume percent excluding additives, obtained by suspending the barium powder preparation according to the first aspect of the present invention in water, having an apparent viscosity ($\eta_{ap}$) of 70 to 250 cp, a yield value ($Y_0$) of 1.5 to 6.6 dyne/cm$^2$, a dynamic modulus (G') of 5 to 19 dyne/cm$^2$, and a dynamic loss (G") of 1 to 6.2 dyne/cm$^2$.

occasionally high at 30 dyne/cm$^2$, causing slightly excess adhesion. A more preferable barium density is 260 W/V%, where the yield value and G" are 5 dyne/cm$^2$ or less and apparent viscosity is 70 cp, showing a visco-elasticity that makes the suspension smooth and ideal for drinking. A few well-known recently commercialized products which claim high densities (HD), having super-high barium densities from 200 to 250 W/V%, have problems such as instability of suspension that may easily produce sludge, and excessive adhesion to the gastric wall, making them inadequate for the upper gastrointestinal double contrast method. The suspension stability of the extremely high density barium of the present invention is outstanding, making almost no sludge. Even if it ever does after maintained still for a few days, it easily becomes uniform when stirred for one or two minutes. Rheologically, it forms a scaffolding structure and, therefore, does not easily precipitate. At an extremely high density of 280 to 290 W/V%, which is close to the maximum, the apparent viscosity is low enough for drinking although a relatively thick layer is formed when the amount of secretion is small. When the barium is applied to patients with excess secretion, it still maintains adequate adhesion and may achieve better visualization of area gastricae, probably due to dilution.

A third aspect of the present invention is an extremely high density barium suspension for upper gastrointestinal examination, wherein a drop of the extremely high density barium suspension according to the second aspect of the present invention causes no visible agglutination when added to a hydrochloric acid solution of pH 1.2 in a petri dish and agitated completely by horizontal circular motions of the petri dish (acid resistance test).

No agglutination should be visible as checked in reference to distilled water (pH not specified) placed in a petri dish, in which a drop of the sample is added and agitated in the same manner. The criterion is far less strict in the conventional comparison method by H. Shirakabe, which stipulates a pH range of 1.3 to 3.95 and no agitation or reference (neutral water such as distilled water). In the acid resistance test of the suspensions of commercially available powder (200 W/V% or less) and sol agents (145 to 100 W/V%), only three products from Fushimi Seiyakusho (Baritogen and Umbrasol, 174 W/V%, and Baritogen DX, 140 W/V%) passed the test with no agglutination, proving the exceptional strictness of the test method.

A fourth aspect of the present invention is a process for producing the barium powder preparation according to the first aspect of the present invention, wherein the large, medium and small component particles are produced according to the procedure consisting of (A) through (C) described later, mixed completely at a weight ratio of [large component particles]:[medium component particles]:[small component particles]=2:1:1 using a V-type mixer, crushed to disperse any resulting coagulation of particles using an atomizer (e.g., an atomizer made by Fuji-PAUDAL), and wrapped as necessary.

When selecting the weight ratio of [large component particles]:[medium component particles]:[small component particles]=2:1:1, the following experiment was conducted. The three types of particles were mixed at various ratios in search of the ratio of the optimum (apparent) viscosity reduction effect and, at the same time, visualization of area gastricae when used as a contrast medium. This procedure is far more complicated than simply seeking a combination that physically attains the maximum viscosity reduction effect. After about 700 cycles of preparation and clinical examinations, it was found that the best mix differed by density. That is, at extremely high densities (260 to 290 W/V%), a ratio of [large particles]:[medium particles]:[small particles]=4:2:2 as in the present invention was suitable; at high densities (160 to 200 W/V%), a ratio of 3:4:2 gave a better result. The 174 W/V% product which did not show agglutination in the acid resistance test, Baritogen, devised also by the inventor, has a ratio of [large particles]:[medium particles]:[small particles]=3:4:2. Note that its particles are not the component particles, as they are coated with higher contents of additives.

If the weight ratio of [large component particles]:[medium component particles]:[small component particles]=2:1:1 is changed slightly to, for example, 1.9:1:1 or 2.1:1:1, deviate from the ratio of maximum viscosity reduction effect, the apparent viscosity reduction effect is not maximized. Furthermore, the contents of the small and medium component particles in the suspension of large, medium and small particles increase or decrease according to the change in the large component particle content. At increased small and medium particle contents (large particle=1.9), for example, G', G" and yield value, particularly the latter two, of the aforementioned four visco-elastic coefficients that are related to visualization increase beyond the allowable limit of the properties given in the second aspect, thus increasing a risk of excessive adhesion of barium to the mucus and fuzziness. Experience has told that a slight increase in the small particle content would increase G' and G". On the other hand, decreased small and medium particle contents (large particle=2.1) would result in the drop of G', G" and yield value, thus increasing the risk of insufficient adhesion to the gastric mucus. Also, when proportions of the medium and small component particle to the large component particles change to 2:1±0.1:1 or 2:1:1±0.1, or to more complicated figures such as 2:1±0.1:1±0.1, the above four visco-elastic coefficients either slightly increase or greatly decrease, and hardly have a possibility to decrease by an adequate amount, which is more preferable. In other words, any deviation from the ratio of 2:1:1 would produce complex effects depending on the relative proportions of the three types of component particles and the visco-elastic coefficients. Practically, therefore, it would be better not to change the ratio. Since the evaluation involved clinical examination, experimenting a combination with unpredictable effects was not practicable. Thus, the ratio of the component particle contents not only has little allowance in variation, but depends on the density as well.

(A) The method for producing the large component particles consists of (1) through (4) below:

(1) A composite additive is prepared, wherein the Gum Tragacanth content and Carrageenan content in the large particles of pure barium sulfate are 0.015% and 0.15%, respectively, their ratio being 1:10, and the effective Gum Tragacanth content, 0.075%, achieves the maximum viscosity reduction effect of the large particles. As shown in Table 2, which indicates the values for the original large particles having a distribution with its peak at 8 $\mu$m, the effective Gum Tragacanth content is used as the reference in determining the contents of the three types of component particles according to their specific surface areas. The contents are determined according to the relatively small specific surface area of the large particles, 0.23 $m^2$/g. and, therefore, are much smaller than in the powder agents in the prior art. The effective Gum Tragacanth content of the three types of component particles per 1 $m^2$ specific surface area is calculated at 0.00325 g, or slightly greater than 3 mg.

(2) Next, the composite additive consisting of Gum Tragacanth and Carrageenan is allowed to swell by adding distilled water accounting for 80±5% of the total water amount necessary for the kneading process in (3) below (13.5±1 wt % of the original large particles) to said composite additive, and conditioning for 24 to 30 hours at room temperature (1 to 30° C.). If the dwell time is less than 24 hours, swelling may be insufficient in winter. If it exceeds 30 hours, the mixture may putrefy and degrade in the midst of summer. The remaining 20±5% distilled water is to be stored for use after the swelling is completed, for washing out the composite additive adhering to the container when it is transferred to the kneader, or for spraying to moisten the pure barium sulfate used as the material at the beginning of kneading when it is too dry.

(3) The large particles of pure barium sulfate, the swollen composite additive described above, and distilled water making up for the remaining portion of the total water amount is transferred, in this order, into a kneader, and kneaded for 90±5 minutes under the following conditions:

The temperature should be controlled so that, if kneading is started at 25±5° C., the kneading gradually increases the mechanical load of the kneader and causes liquidization at the peak thereof, and, if the kneading is continued adequately after the liquidization, the temperature increases gradually to 33±2° C. and remains as is or decreases slightly. The temperature deviation of ±2° C. allows for seasonal variations in the ambient temperature and humidity. Liquidization occurs (the kneader ammeter indication drops) after 40±5 minutes of kneading. However, an additional 40 minutes or more of kneading is necessary to attain the desired viscosity reduction effect.

(4) Then, distilled water is added to the pasty large component particles obtained by the kneading, to make a 100±10 W/V% aqueous suspension, which is then heated to dry and sterilize on the wall of a rotating drum dryer, to obtain the large component particles as powder. The drum dryer specifications may be, for example, a diameter of 52 cm, a width of 50 cm, a rotation speed of ½ rpm, a drum surface temperature of 130° C. or above; however, they may vary depending on the quantity of production and the dryer size. The aqueous suspension is to be applied to the dryer by dripping through many small pores, bringing into contact with its bottom, or by any other appropriate manner for the quantity to be processed.

(B) The method for producing the medium component particles consists of (1) through (4) below:

(1) A composite additive is prepared, wherein the ratio of the Gum Tragacanth content and Carrageenan content in the medium particles of pure barium sulfate is 1:9±1, and the ratio of the effective Gum Tragacanth content in the large particles (0.075% in the large component particles) and the effective Gum Tragacanth content in the medium particles is identical to the ratio of the specific surface areas of the large and medium particles.

The ratio of the specific surface areas of the large and medium particles varies between 1:2.8 to 1:3.3 due to the variation in the particle size of the medium particles, as mentioned earlier. Accordingly, the effective Gum Tragacanth content (0.075%×2.8 to 3.3 in the large component particles) in the medium particles selected according to this ratio also varies between 0.21% to 0.25%. The effective Gum Tragacanth content per 1 m² specific surface area is calculated at 0.00326 g for the medium particles, as for the large particles.

(2) Next, the composite additive consisting of Gum Tragacanth and Carrageenan is allowed to swell by adding distilled water accounting for 80±5% of the total water amount necessary for the kneading process in (3) below (15±1 wt % of the original medium particles) to said composite additive, and conditioning for 24 to 30 hours at room temperature (1 to 30° C.). If the dwell time is less than 24 hours, swelling may be insufficient in winter. If it exceeds 30 hours, the mixture may putrefy and degrade in summer. The remaining 20±5% distilled water is to be stored for use after the swelling is completed, for washing out the composite additive adhering to the container when it is transferred to the kneader, or for spraying to moisten the pure barium sulfate used as the material at the beginning of kneading when it is too dry.

(3) The medium particles of pure barium sulfate, the swollen composite additive described above, and distilled water making up for the remaining portion of the total water amount is transferred, in this order, into a kneader, and kneaded for 60±5 minutes under the following conditions:

The temperature should be controlled so that, if kneading is started at 25±5° C., the kneading gradually increases the mechanical load of the kneader and causes liquidization at the peak thereof, and, if the kneading is continued adequately after the liquidization, the temperature Increases gradually to 37±2° C. and remains as is or decreases slightly. The temperature deviation of ±2° C. allows for seasonal variations in the ambient temperature and humidity. Liquidization occurs (the kneader ammeter indication drops) after 20±5 minutes of kneading, earlier than in the large particles. However, an additional 40 minutes or more of kneading is necessary to attain the desired viscosity reduction effect. Kneading that extends somewhat longer after liquidization simply makes the rotation loose and the frictional resistance low, and causes little problem as long as the temperature does not rise.

(4) Then, distilled water is added to the pasty medium component particles obtained by the kneading, to make a 100±10 W/V% aqueous suspension, which is then heated to dry and sterilize on the wall of a rotating drum dryer, to obtain the medium component particles as powder. Processing with the drum dryer is the same as in the production of the large component particles described earlier.

(C) The method for producing the small component particles consists of (1) through (4) below:

(1) A composite additive is prepared, wherein the ratio of the Gum Tragacanth content and Carrageenan content in the small particles of pure barium sulfate is 1:0.9±0.1, and the ratio of the effective Gum Tragacanth content in the large particles (0.075% in the large component particles) and the effective Gum Tragacanth content in the small particles is identical to the ratio of the specific surface areas of the large and small particles.

The ratio of the specific surface areas of the large and small particles varies between 1:6.9 to 1:7.5 due to the variation in the particle size of the small particles, as mentioned earlier. Accordingly, the effective Gum Tragacanth content (0.075%×6.9 to 7.5 in the large component particles) in the small particles selected according to this ratio also varies between 0.52% to 0.56%. The effective Gum Tragacanth content per 1 m² specific surface area is calculated at 0.00329 g for the small particles, as for the medium and large particles. (The disagreement at the fifth place of decimals is attributed to the errors in the measured values used for the calculation.)

(2) Next, the composite additive consisting of Gum Tragacanth and Carrageenan is allowed to swell by adding distilled water accounting for 80±5% of the total water amount necessary for the kneading process in (3) below (15±1 wt % of the original small particles) to said composite additive, and conditioning for 24 to 30 hours at room temperature (1 to 30° C.). If the dwell time is less than 24 hours, swelling may be insufficient in winter. If it exceeds 30 hours, the mixture may putrefy and degrade in summer. The remaining 20±5% distilled water is to be stored for use after the swelling is completed, for washing out the composite additive adhering to the container when it is transferred to the kneader, or for spraying to moisten the pure barium sulfate used as the material at the beginning of kneading when it is too dry.

(3) The small particles of pure barium sulfate, the swollen composite additive described above, and distilled water making up for the remaining portion of the total water amount is transferred, in this order, into a kneader, and kneaded for 90±5 minutes under the following conditions:

The temperature should be controlled so that, if kneading is started at 25±5° C., the kneading gradually increases the mechanical load of the kneader and causes liquidization at the peak thereof, and, if the kneading is continued adequately after the liquidization, the temperature increases gradually to 40±2° C. and remains as is or decreases slightly. The temperature deviation of ±2° C. allows for seasonal variations in the ambient temperature and humidity. Liquidization occurs (the kneader ammeter indication drops) after 25±5 minutes of kneading, slighter later than in the medium particles. However, the temperature rise is greater than in the large and medium particles explained before. An additional 60 minutes or more of kneading is necessary to attain the desired viscosity reduction effect.

Kneading that extends somewhat longer causes little problem as long as it is simply loose rotation with low frictional resistance and the temperature does not rise. However, excessive kneading is not recommended, because the small size of the particles may produce larger internal frictional resistance during kneading. Precaution against excessive kneading is necessary.

(4) Then, distilled water is added to the pasty small component particles obtained by the kneading, to make a 100±10 W/V% aqueous suspension, which is then heated to dry and sterilize on the wall of a rotating drum dryer, to obtain the small component particles as powder. Processing with the drum dryer is the same as in the production of the large and medium component particles described earlier.

FIG. 2(A) shows an example of the temperature of the small particles during kneading as a function of time. FIG. 2(B) shows an example of the temperature of the medium particles during kneading as a function of time. FIG. 2(C) shows an example of the temperature of the large particles during kneading as a function of time.

A fifth aspect of the present invention is a process for preparing the extremely high density barium suspension for upper gastrointestinal examination according to the second aspect of the present invention, wherein the barium powder preparation according to the first aspect of the present invention is mixed with and suspended in a specified amount of water.

Table 7 given later will show examples of the range of density, the amount of water in milliliters to be added to make a suspension per 100 g of the barium powder preparations of the present invention, and the apparent viscosity ($\eta_{ap}$) of the extremely high density barium suspension of the present invention.

A sixth aspect of the present invention is a novel and easier method of X-ray upper gastrointestinal examination than in the prior art, wherein the extremely high density barium suspension according to the second aspect of the present invention is used as a contrast medium for double contrast method.

Furthermore, a seventh aspect of the present invention is a method of X-ray upper gastrointestinal examination according to the sixth aspect of the present invention without the use of a gastric tube and any parasympathicolytic. This method of examination of the present invention is a new X-ray examination method that significantly reduces the stress on the patient.

BRIEF DESCRIPTION OF THE DRAWINGS

FIGS. 2(A), 2(B) and 2(C): are diagrams showing the temperatures of the small, medium and large particles during kneading, respectively, as functions of time.

FIG. 7 is the frequency dependent curves for G', G" and $\eta$' of the extremely high density barium suspension according to the present invention.

DETAILED DESCRIPTION OF THE PREFERRED EMBODIMENTS

Figure 1:
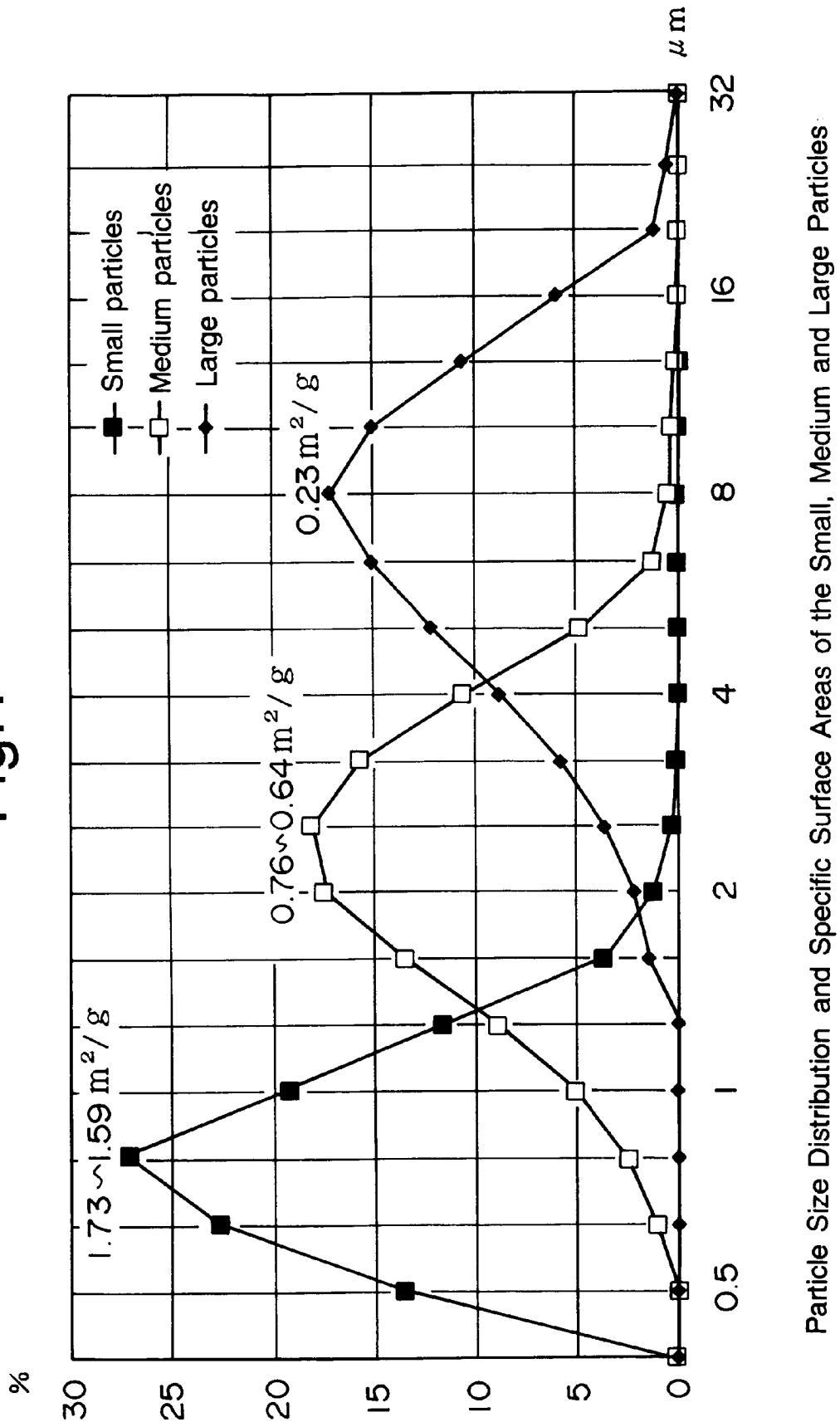
FIG. 1 is a diagram showing the particle size distribution and specific surface areas of the small, medium and large particles.

In the present invention, the large, medium and small particles of the pure barium sulfate used as the material needs to be mixed individually with specified amounts of composite additives consisting of specified proportions of Gum Tragacanth and Carrageenan, and kneaded under specified conditions, in order to fragment adequately the molecules of the Gum Tragacanth and Carrageenan and coat the particles with them, to make the viscosity as low as possible. The large, medium and small particles, whose viscosity has been lowered, are referred to as large component particles, medium component particles, and small component particles, respectively. They are to be mixed at an appropriate ratio to give a further low viscosity according to the Roller theory, which will be explained later.

Pure barium sulfate used in the present invention is insoluble particles with a specific gravity as high as 4.5. To make it a stable and unprecipitable suspension with high density and low viscosity, the intrinsically negative (−) surface charge ($\zeta$ potential) of the particles needs to be changed to positive (+) by coating with an appropriate additive. By doing so, agglutination of the particles can be suppressed, while the barium suspension can be made extremely stable in an acidic medium containing hydrogen ions ($H^+$), i.e., in the strongly acidic environment in the stomach with a pH as low as 1.2.

The most suitable additives to be used for that purpose are Gum Tragacanth and Carrageenan, which are natural polysaccharides as described before. The question is the condition of coating. An ideal condition would be that the molecules of the additive coat the particle surface completely via Van der Waals' force while they remain little in the water used as a dispersant. Most common natural polysaccharides are Gum Arabic and starch, which are known to function as glue. Here, glue shall refer to a condition where the dispersed system in sol has lost its fluidity and gelled to become a highly viscous state.

Gum Tragacanth and Carrageenan have much greater molecular weights than other materials such as Gum Arabic. Therefore, even if they remain in small amounts in the dispersant water, the viscosity of the suspension increases. It is ironical that the additive used to reduce the viscosity and stabilize the suspension increases the viscosity when remaining in the dispersant water. All the barium products in the prior art, hardly called an ideal mixture, contain excess glue component in the dispersant and, thus, have unnecessarily high viscosities.

Bottled sol agents with barium densities of 100 to 150 W/V%, in particular, contain relatively large amounts of glue component in the dispersant to extend the suspension stability. Constipation, a common side effect of barium, is primarily due to the excess amount of additive contained in the dispersant. When barium reaches the large intestine and is subject to strong physiological water deprivation, the remaining glue component condenses the barium particles into various sizes of rock-solid clusters like rabbit's stool.

Characteristics of Gum Tragacanth

Gum Tragacanth is a water-soluble pasty material that seeps out of the trunks of bushes of Astragalus species in the semi-desserts of Iran, Syria, Turkey and other Middle and Near East countries, and is available as dry resin. It is graded by quality. The thin whitish "ribbons" of 5 to 10 cm with high quality with little impurities are graded high at Nos. 1 to 6. No. 1 has long 4500 Å×19 Å molecules with molecular weights as high as 800,000 or above and, thus, high viscosities of about 300 cp. The brown, thick and fragile "flakes" of 1 to 5 cm have lower quality and contain large amounts of impurities. They are graded at Nos. 26 to 28 and have lower viscosities of about 100 cp.

For the present invention, it is recommended to use No. 1 ribbons, which are first class Gum Tragacanth (molecular weight: 840,000). These highest quality ones are available chiefly in Iran and Iraq. However, the quality grade has nothing to do with origins. Recently, the price has increased, making it difficult to use the material as food additives. When high class Gum Tragacanth such as No. 1 is used as an additive, the dynamic modulus (G') of the barium suspension rises extraordinarily, although the apparent viscosity drops considerably. This steep increase of G' may result in excessive adhesion to the mucosa and, therefore, the formation of an unnecessarily thick layer.

Gum Tragacanth is composed mainly of Tragacanthic acid and Bassorin, as well as of water (10%), cellulose (4%), starch (3%), and minerals (3%). The main component, Tragacanthic acid, is a mixture of acidic polysaccharides consisting of fucose, xylose, and galacturonic acid, and neutral polysaccharides consisting of galactose and arabinose. Bassorin is an acidic polysaccharide having a methyl group. It is believed that Tragacanthic acid is produced by the demethylation of Bassorin. Bassorin, accounting for 60 to 70% of Gum Tragacanth, is water-insoluble and swells to become gel. Tragacanthic acid is water-soluble and forms hydrophilic colloidal sol. Gum Tragacanth shows structural viscosity (non-Newtonian) in an aqueous solution with a concentration of 0.5% or higher. Crushed ribbons or flakes may show a decreased viscosity, presumably because the mechanical shock produces fissuring in the molecular chain structures. This fact implies the significance of kneading in the present invention, as it is reasonably expected that mechanical shocks of kneading would produce similar fissuring in the molecular structures.

Characteristics of Carrageenan

Carrageenan, extracted from Gigartinales Rhodophyta such as Gigartina, Chondrus, Iridaea and others by water, is a polysaccharide whose chemical structure is chained pairs of galactose molecules. It is white to light beige powder with a lower molecular weight and viscosity than those of Gum Tragacanth. Generally, it is composed of three different fractions, i.e. κ, λ and ι, and rarely of a single structure. The molecular weight, ranging normally from 100,000 to 800,000, is larger in the λ fraction than in the κ fraction.

An example of Carrageenan suitably used for the present invention is Jenugel CJ (Copenhagen Pectin Co., Inc.), in which λ fraction accounts for about ⅓ of the Carrageenan content. It is a gelled mixture intended originally for fruit jelly and contains a large amount of impurities as proved by analysis. As λ-Carrageenan hardly contains 3,6-anhydro group, it is not easily gelled or affected by cations ($K^+$ or $Ca^{++}$) and has low elasticity. In other words, it is significantly inferior in viscosity reduction effect to Gum Tragacanth, but does not raise the dynamic modulus (G') as excessively as Gum Tragacanth. To use in addition to Gum Tragacanth, low-molecular weight mixture containing a modest amount of impurities that does not excessively raise the dynamic modulus (G') of the barium suspension seems suitable, rather than pure κ-, λ- or κι-Carrageenan with high molecular weights. This consideration is similar to what applies when discussing the character of medicines: A crude drug may sometimes be superior in practice because of its milder pharmacological effect than a pure synthetic cardiac.

Table 3 shows the classification and characteristics of Carrageenan.

TABLE 3

Classification and Characteristics of Carrageenan

| | κ-Carrageenan | λ-Carrageenan | ι-Carrageenan |
|---|---|---|---|
| Galactose | 29% approx. | 45% approx. | 20% approx. |
| Sulfuric group | 26% approx. | 35% approx. | 31% approx. |
| 3,6-anhydro group | 29 to 28% approx. | 0 to 2% approx. | 20 to 30% approx. |
| Effect of cations | Gelled most effectively by K ion | Not gelled by K ion | Gelled most effectively by Ca ion |
| Characteristics of gel | Fragile, Large water releasable heat-reversible | Not gelled | Elastic, Small water releasable, heat-reversible |
| Solubility to cold water | Swells but insoluble. Sodium salt is soluble. | All metallic salts are soluble. | Calcium salt makes thixotropic dispersion. |
| Major component sugars | D-galactose, 4-sulfuric-3, 6-anhydro-D-galactose | D-galactose, 2-sulfuric-D-galactose 2,6-disulfate | D-galactose, 4-sulfuric-3, 6-anhydro-D-galactose 2-sulfate |
| Suitable applications | Jelly; gelling Ice cream; thickening Condensed milk; fat stabilization Chocolate milk; suspension | Syrup; thickening and dispersion Coffee cream; emulsion stabilization | Jelly; gelling Condensed milk; fat stabilization Canned and other foods; gelling Aromatic agents; gelling |

Composite Additive Consisting of Two Polysaccharides

Gum Tragacanth and Carrageenan, both of which are natural polysaccharides having long chain structures, may be used as additives in combination in a ratio where their characteristics are maintained, to significantly reduce the apparent viscosity while preventing excessive increase of the dynamic modulus (G') and thereby to produce a barium suspension that is smooth and forms a thin layer. The former serves to reduce the apparent viscosity most effectively, whereas the latter helps reduce dynamic coefficients such as dynamic modulus (G') and dynamic loss (G"). By adding these two substances in combination to the original large, medium and small particles in a ratio to maximize their advantages, the component particles can be provided with the optimum visco-elastic characteristics as a contrast medium.

Contents Determined by Specific Surface Areas of Original Particles

The surface area per unit weight of the particles, i.e., the specific surface area, steeply increases as the particle size decreases. Higher content is necessary for smaller particles, while large particles only require very small contents. Therefore, it is important to determine the content precisely in proportion to the specific surface areas of the large, medium and small particles calculated using the measured particle size distribution of the original particles.

Effective Gum Tragacanth Content

The present invention assumes that Gum Tragacanth has a viscosity reduction effect that is 2.5 times that of Carrageenan, when determining the effective Gum Tragacanth content of the composite additive. This assumption is based on the calculation that, taking the molecular weight of the aforementioned Jenugel CJ Carrageenan as 330,000, the proportion of the molecular weight of the aforementioned No. 1 Gum Tragacanth, 840,000, is 2.5.

An example of the calculation of the effective Gum Tragacanth content is as follows (see Table 2 for the results of calculation): In the large particles, the content of Gum Tragacanth and Carrageenan are 0.015% and 0.15%, respectively (ratio of contents of Gum Tragacanth and Carrageenan is 1:10), the effective Gum Tragacanth content for Carrageenan is 0.15%/2.5=0.06%. Thus, the effective Gum Tragacanth content of the composite additive in the large particles is 0.015%+0.06%=0.075% (see Table 2).

The ratio of the effective Gum Tragacanth contents of the three types of particles is identical to the ratio of their specific surface areas. When the ratio is [large particles]: [medium particles]:[small particles]=1:3.3:7.5, the effective Gum Tragacanth contents of the medium and small particles are 3.3 times and 7.5 times, respectively, that of the large particles. Hence, the effective Gum Tragacanth content of the medium particles is 0.075%×3.3=0.25%, and that of the small particles is 0.075%×7.5=0.5625% (rounded to 0.56%).

In the medium particles, the ratio of the Gum Tragacanth content and the Carrageenan content is approximately 1:10. Therefore, in order to attain the effective Gum Tragacanth content of the medium particles, 0.25%, the Gum Tragacanth content in the medium particles must be 0.05% and the Carrageenan content 0.5%.

In the small particles, the ratio of the Gum Tragacanth content and the Carrageenan content is approximately 1:1. Therefore, in order to attain the effective Gum Tragacanth content of the small particles, 0.56%, the Gum Tragacanth content in the small particles must be 0.4% and the Carrageenan content 0.4%. All contents above are expressed in wt %.

Kneading Method

In the present invention, three sizes of pure barium sulfate particles, i.e., large, medium and small, are mixed with an appropriate amount of water and kneaded with an appropriate amount and composition of composite additives using a kneader for an appropriate time at an appropriate temperature. Checking for liquidization and continued kneading thereafter are important. During kneading, the proportion and content of the composite additive, the amount of water, the kneading time, the temperature, and other conditions are to be selected differently from the large, medium and small particles. By doing so, the additive content can be reduced to ½ to ⅓ of that the barium in the prior art while achieving a dramatic viscosity reduction effect.

As shown in Table 4, the apparent viscosities of the component particles of the present invention are hundredths to a seventh, dramatically low, of those of the commercial barium. The kneading method according to the present invention has an unparalleled viscosity reduction effect.

TABLE 4

Comparison of Viscosity between the Component Particles and Commercial Barium Products
(*Products having roughly similar particle size distribution
to that of the component particles are used as references.)

| | Present invention | | | Commercial barium products (unmixed particle sizes) | | | |
|---|---|---|---|---|---|---|---|
| Component particles | Additives | Effective Gum Tragacanth content | $\eta_{ap}$ (cp) | Particles | Tradename | Year of production | $\mu_{ap}$ (cp) |
| Large particles | G & C | 0.075% | 16 | Large | Baritogen DXH10 (Lot. 003234)*[1] | 1990 | 140 |
| | | | | | Mikabarium $B_{12}$ (Lot. KE22)*[2] | 1971 | 500 |
| | | | | | Bestbar P (Lot. unknown)*[3] | 1968 | 1500 |
| Medium particles | G & C | 0.21% | 18 | Medium | Baritogen DX (Lot. 203050) 167 W/V %*[4] | 1972 | 250 |
| | | | | | Baritogen DX (Lot. 060711) 167 W/V %*[5] | 1990 | 182 |
| | | | | | Umbrasol A (Lot. 74951504)*[6] | 1987 | 38 |
| | | | | | Umbrasol A (Lot. 912147)*[7] | 1989 | 50 |
| Small particles | G & C | 0.56% | 20 | Small | Barosperse (Lot. HP10213) 160 W/V %*[8] | 1971 | 152 |
| | | | | | Baritop P (Lot. 7116) 164 W/V %*[9] | 1977 | 90 |

*G: Gum Tragacanth, C: Carrageenan
*50 g barium powder + 17 ml water for all samples (174 to 163 W/V % approx.)
*[1] & *[4]–*[7]: manufactured by Fushimi Seiyakusho Co. Ltd.
*[2], *[3] & *[9]: manufactured by the other manufactures in Japan.
*[8]: Mallinckrodt Inc., made in U.S.A.

Structure of the Kneader

Figure 3A:
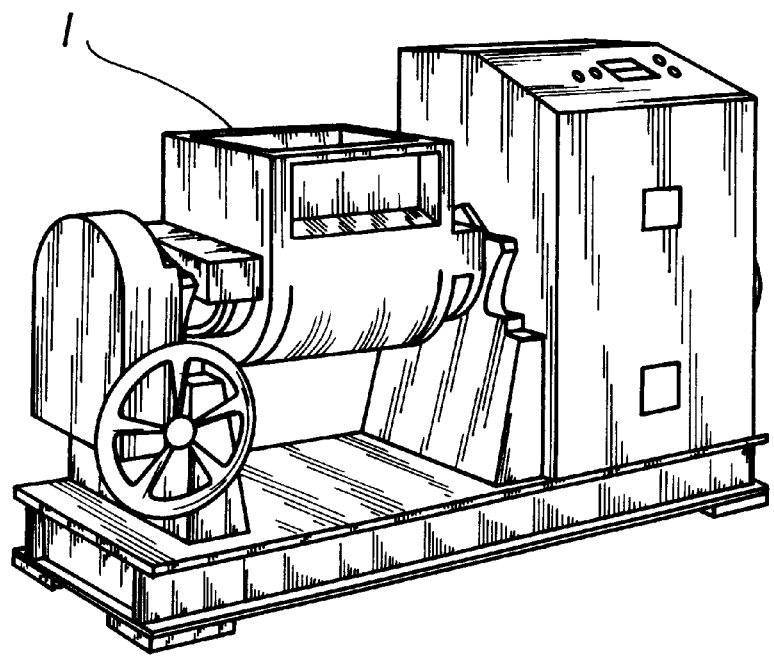
FIG. 3(A) is a perspective view showing the appearance of the kneader and FIG. 3(B) is an explanatory view showing the inside of the kneading chamber as turned over.
Figure 3B:
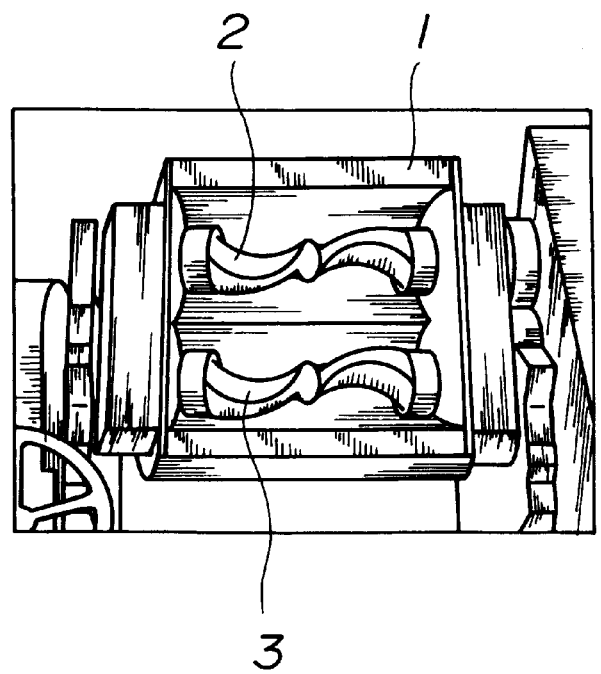

Kneading according to the present invention is physical kneading by a kneader. FIG. 3(A) shows the perspective view of the kneader appearance, and FIG. 3(B) shows the inside of the most essential part, the kneading chamber 1, in which two blades (Σ-type) 2 and 3 that rotate in opposite directions knead the mixture. A three-phase AC motor (not shown) on the right gives rotating torque via reducing gears (not shown) to the two blades 2 and 3. The rotation speeds of the blades are unequally set at about 50 to 26 rpm. The two blades 2 and 3 rotate at different speeds to prevent the mixture from being gathered to one place and keep uniformity. The kneading chamber 1 has a capacity of, for example, 3.8 liters in small kneaders, 20 liters in medium kneaders, and 60 liters in large kneaders, all of which are for experimental use. Industrial kneaders with a capacity of 300 liters have essentially the same structure, except that the kneading chamber is turned over electrically, instead of manually as in the experimental ones. The 60 liter large experimental kneader can accommodate small particles of pure barium sulfate up to about 30 kg.

Specificity of the Kneading Method

The primary reason why the viscosity can be lowered as mentioned above is that an exactly necessary amount of additives cover the particle surface. In other words, the water used as the dispersant of the suspension contains almost no additive, or no glue component, making it smoother than in the prior art even at extremely high densities and easier to flow on the gastric wall.

Rheologically, the barium is "characterized" by a yield value of 1.5 to 6.6 dyne/cm$^2$, a low dynamic loss (G") and a dynamic modulus (G') of 1 to 6.2 dyne/cm$^2$ and 5 to 19 dyne/cm$^2$, respectively, at a moving rate of 0.55 Hz, and an apparent viscosity of a moderate 70 to 250 cp, and has a flow curve which shows low yield value, thixotropy with a counterclockwise hysteresis loop, and so closely approximates to Newtonian flow, at barium sulfate densities of 260 to 290 W/V%. The barium has a very low yield value and G" of 7 dyne/cm$^2$ or less and, therefore, is perceived to be extraordinarily smooth when clinically applied to gastric contrast examination.

Furthermore, when the barium containing little glue component in the dispersant reaches the large intestine, it is not easily condensed under the physiological water deprivation. In other words, unlike the barium in the prior art containing lots of glue component, the barium does not lose fluidity after the water deprivation in the large intestine which may raise the barium density to as high as 290 W/V% or above, significantly lessening the risk of constipation. Also, old patients above 80 years of age may accidentally suck barium through the trachea into the lung. If this happens, barium that has reached the depth of the lung is not easily spit out, even presenting a bronchogram and causing a secondary infectious disease such as pneumonia, which may develop to a grave condition. Even if the patient can be saved from the immediate danger, the glue-rich barium in the prior art may adhere to the alveoli at the depth of the lung and remain for life. The barium according to the present invention, even after such accidental suction, can be removed from the lung almost completely within 3 to 4 hours only by taking an appropriate treatment promptly, such as the administration of an expectorant. This is because, as exemplified by the constipation in the large intestine, the barium does not lose its fluidity even after water deprivation to an almost dry state, because of its low glue content and, thus, is easy to spit out by the administration of an expectorant.

Comparison between the Kneading Method and the Method of Addition in the Prior Art To use additives in barium, so-called "wet addition" has been implemented for a long time. Up to the 1930's, products were not like what they are today. Doctors had to prepare barium themselves before a contrast examination, by mixing Gum Tragacanth and Gum Arabic with pure barium sulfate powder in a bowl and kneading them with a pestle, while adding water little by little. The term "barium meal," common in those days, well represents the low fluidity of the medium.

Table 5 shows the comparison of the apparent viscosity, yield value, and the result of the acid resistance test between barium produced by the kneader according to the present invention and by the homogenizing mixer, which is another typical device for addition. About 175 W/V% barium suspension samples were constantly prepared from 50 g of barium powder and 17 ml of water to compare the viscosity reduction effect.

The medium component particles according to the present invention (Gum Tragacanth content: 0.05%; Carrageenan content: 0.4%) and the two barium samples prepared by a homogenizing mixer, i.e., Baritogen DX (Gum Tragacanth content: 0.5% approx.) and Umbrasol-A (chondroitin sulfate content: 1 to 2% approx., equivalent to an effective Gum Tragacanth content of 0.5 to 1.0% approx.), shown in Table 5 were all produced using the medium particles of pure barium sulfate from the same manufacturer (Fushimi Seiyakusho Co., Ltd.).

1) A homogenizing mixer is a device in which a large amount of hot water (80° C.) is mixed with pure barium sulfate and additives such as Gum Tragacanth and chondroitin sulfate, and a steel blade turbine rotating at a high speed (3600 rpm) produces a shearing force by a strong jet in a stator suspended in the mixture to agitate it. Baritogen DX and Umbrasol-A were both produced by using a homogenizing mixer. Baritogen DX contains No. 1 Gum Tragacanth as a primary additive and, therefore, just throwing in the Gum Tragacanth would not produce a good result because of its long chain structure with a molecular weight of 840,000. Therefore, the addition of NaOH is necessary to chemically cut the molecules. Also, long (at least 8 hours continuously) and intense agitation by jet in a hot chamber (80° C. or above) is required.

In the kneading method, however, the strong shearing force produced by kneading cracks the long chains of molecules physically, eliminating the necessity for a pre-treatment and heating during kneading, while shortening the process time (90±5 minutes or less).

As shown in Table 5, Baritogen DX produced by a homogenizing mixer has an apparent viscosity of 128 cp. As compared to the 18 cp of the medium component particles according to the present invention produced by the kneading method, the viscosity reduction effect is only 1/7.5. The Gum Tragacanth content in the medium component particles is 0.05%. When the content of the Carrageenan used in combination, 0.4%, is taken into consideration, the effective Gum Tragacanth content is still 0.21%.

The Gum Tragacanth content of Baritogen DX is about 2% or less. Assuming the minimum possible content as 0.5%, Baritogen DX still requires more than twice as much Gum Tragacanth as the medium component particles.

In the medium component particles, the use of the expensive Gum Tragacanth can be reduced to 1/10 of that in Baritogen DX. Therefore, even though the additional use (0.5%) of the relatively inexpensive Carrageenan (see aforementioned Jenugel CJ) is required, the total cost of the additives for the medium component particles produced by the kneading method is still about ⅓ of that required in the homogenizing mixer method.

The yield value of the medium component particles produced by a kneader is zero, as measured by a precise cone-plate type rheometer, as shown in Table 5, much smaller than the 7.9 dyne/cm of Baritogen DX produced by a homogenizing mixer. The yield value cannot be too low in a contrast medium. The apparent viscosity of Umbrasol, which is produced from the same material as the medium component particles, is 50 cp, as compared to the 18 cp of the medium component particles, with a viscosity reduction effect of about ⅓ of that of the medium component particles. The pure barium sulfate content of Umbrasol is the lowest at 96% of all the products, with an assumed content of chondroitin sulfate, which is the primary additive, of 1 to 2%.

Therefore, the calculated effective Gum Tragacanth content is about 0.5 to 1.0%. This is about three times that of the medium component particles produced by a kneader, which has an effective Gum Tragacanth content of 0.21%. Umbrasol has a very low yield value at 3.5 dyne/cm$^2$, less than half that of Baritogen DX, but still much higher than zero of the medium component particles produced by a kneader. Also, in the acid resistance test, the medium component particles produced by a kneader did not coagulate at all (shown as (−) in Table 5), while Baritogen DX produced by a homogenizing mixer did coagulate slightly (shown as (±) in Table 5).

TABLE 5

Comparison of Products by Kneader and Homogenizing Mixer

| Method of addition | Kneader Medium component particles | Homogenizing mixer | |
|---|---|---|---|
| | | Baritogen DX | Umbrasol-A |
| Apparent viscosity (cp) | 18 | 128 | 50 |
| Yield value (dyne/cm$^2$) | 0 | 7.9 | 3.5 |
| Acid resistance test | (−) | (±) | (−) |

2) Dry-spray is another common way of addition, in which additives are resolved in volatile organic solvent and mixed with a diluted suspension of pure barium sulfate used as the material, sprayed through pores at a high pressure into hot air (about 100 to 200° C.) to be atomized and attached to the material particles as they dry. A typical product is Baritop P (tradename, Kaigen Corp.). Baritop P is composed of small particles of 1 μm or less having a comparable particle size distribution to the small component particles of the present invention. The apparent viscosity, yield value, and the result of the acid resistance test as performed at the same density as mentioned above (suspension containing 50 g barium powder per 17 ml of water) are shown in Table 6.

In dry-spray, the apparent viscosity of Baritop P is 110 cp, as compared to the 20 cp of the small component particles, showing a viscosity reduction effect that is only about ⅕ of that of the kneaded product. The yield value is low enough at 2.2 dyne/cm$^2$. However, in the acid resistance test, considerable agglutination was observed, revealing the product's low acid resistance. The small component particles produced by a kneader showed no agglutination in the acid resistance test, while its yield value was low enough at 3.5 dyne/cm$^2$.

TABLE 6

Comparison of Products by Kneader and Dry-Spray

| Addition | Kneader Small component particles | Dry-spray Baritop P |
|---|---|---|
| Apparent viscosity (cp) | 20 | 110 |
| Yield value (dyne/cm$^2$) | 3.5 | 2.2 |
| Acid resistance test | (−) | (+++) |

In sum, the use of a kneader has clear and overwhelming advantages over the other two methods of addition in the prior art in decreasing the apparent viscosity and yield value, and in acid resistance.

Advantages of Small Additive Contents in the Present Invention

The contents of additives stated in the instruction manuals of commercial barium are 2 to 6%, about 10 times higher than that of the present invention. Additives used in commercial barium include, besides the primary additives such as Gum Tragacanth and Carrageenan, sweetener, flavor, osmoregulator, defoamer (silicone), and other supplementary additives. As their contents are normally not disclosed, real composition is unknown. Disclosure of the contents of effective constituents and pure barium sulfate is mandatory. In commercial barium, the content of pure barium sulfate is 99 to 94%. Therefore, the only information available is that the remaining a few percent makes up the additives. It is unrealistically difficult, therefore, to calculate the effective Gum Tragacanth content.

However, major additives that are related to the viscosity of commercial barium are estimated at about 1 to 0.5%, which is why the inventor assumed that only ½ to ⅓ is necessary as mentioned earlier. Note that, however, this estimation is a fairly modest one.

As explained above, smaller amounts of additives are necessary in the present invention, giving it the tremendous edge in production cost. The reduction of running cost becomes remarkable as the production quantity increases. As Gum Tragacanth and Carrageenan used for production are natural materials with limited availability, it is significant that the present invention helps reduce the consumption of these valuable materials and, thus, contributes to the conservation of global resources.

EMBODIMENT

The pure barium sulfate to be used as a material is, as measured by Coulter counter, has a particle size distribution with its peak at 8 μm for the large particles, 2 to 2.5 μm for the medium particles, and 0.8 to 1 μm for the small particles. The particle size distribution of each type of particles, as shown in FIG. 1, needs to be close to normal distribution.

The measured particle size distribution of the original particles is used to calculate the specific surface areas of the large, medium and small particles. With the specific surface area of the large particles taken as 1, the ratio of the large, medium and small particles should be 1:2.8–3.3:6.9–7.5 as shown in Table 2. The ratio of the contents of the additives should be identical to this ratio. Since two additives are used in combination, they should be mixed in such a manner that the effective Gum Tragacanth content which is calculated with the viscosity reduction effect of Gum Tragacanth assumed as 2.5 times that of Carrageenan is identical to the ratio of the specific surface areas. As the medium and small particles vary slightly in particle size by lot, so do their specific surface areas. Therefore, the contents of the additives must be adjusted accordingly, by changing the content of Carrageenan, which has a relatively small molecular weight and a minor effect on the viscosity.

As mentioned in the explanation of the production processes of the component particles, the effective Gum Tragacanth content per 1 $m^2$ surface area is very strictly controlled to 0.00327±0.00002 g, or 3.27±0.02 mg, regardless of the particle size.

The total amount of water necessary for kneading the composite additive in a kneader is 13.5±1 wt % for the large particles, and 15±1 wt % for the medium and small particles. These amounts allow for the water necessary to swell the additives, and for spray to the barium powder when it is too dry due to weather conditions. Therefore, the actual amount to be used during kneading, excluding the spared amount, is relatively small (approximately 20±5% of total water).

Powder of Gum Tragacanth (first class) and Carrageenan (Jenugel CJ, described earlier) is mixed at the ratio specified in Table 2 above for each particle size, mixed with 80±5% of the total amount of distilled water described above, and allowed to swell at room temperature for 24 hours or more (depending on season).

To knead the mixture, the kneader is to be operated while transferring the original particles, swollen additives, and the remaining portion of the distilled water that makes up for the aforementioned total water amount, in this order. The completion of transfer is deemed as the beginning of kneading. The kneading time is 90±5 minutes for the large particles, 60±5 minutes for the medium particles, and 90±5 minutes for the small particles.

During kneading, the mechanical load of the kneader increases gradually and, when it reaches its peak, liquidization begins. Liquidization is observed at 40±5 minutes for the large particles, 20±5 minutes for the medium particles, and 25±5 minutes for the small particles. After the beginning of liquidization, the large and medium particles should be kneaded for an additional about 40 minutes, and the small particles about 60 minutes. To check for the peak of the mechanical load, the AC current of the kneader is to be monitored. For example, it may be 1.6 A at the beginning of kneading, rise to 2.3 A at the peak, and drop to 1.6 A after the completion of liquidization.

The temperature during kneading is 25±5° C. at the beginning, and increases gradually to 40±2° C. for the small particles, 37±2° C. for the medium particles, and 33±2° C. for the large particles. After the peak of the mechanical load is reached and liquidization starts, temperature rises more slowly, then remains as is or drops slightly. A temperature sensor is to be placed on the outside thermostatic lumen of the kneader to record the temperature continuously on a pen recorder for temperature control.

As mentioned earlier, FIGS. 2(A), 2(B) and 2(C) show the temperatures of the small, medium and large particles, respectively, during kneading as functions of time.

The pasty large, medium and small component particles thus obtained by kneading is suspended individually in water to make about 100 W/V% aqueous suspensions, and heated in a drum dryer to dry and sterilize to make dry powder of component particles with little coagulation.

More specifically, the pasty component particles obtained by kneading may be diluted with water to make about 100 W/V% suspensions, then injected for quick drying into a steel drum dryer that has been heated by high pressure steam of 130° C. or above, to obtain well-dispersed dry powder of component particles with little coagulation. It is recommended that the steam pressure and drum rotation speed be controlled to achieve a drum surface temperature suitable for drying and sterilizing the powder. The drum rotation speed is very slow at about ½ rpm.

The ratio of the large, medium and small component particles necessary for making the barium powder preparation of the present invention is [large component particles] :[medium component particles]:[small component particles]=2:1:1 as intended for use at extremely high densities of 260 to 290 W/V%.

To mix the large, medium and small component particles, they need to be processed, for example, in a V-type mixer for 1 hour.

In a final treatment after mixing, the remaining coagulating particles are to be dispersed by letting them through an atomizer (tradename: Sample Mill; Fuji-PAUDAL KII-1 with 2 mm mesh), for example, to obtain the barium powder preparation of the present invention.

In the present invention, the density of a barium suspension in which the barium powder preparation is suspended in water is expressed as weight (g)/volume (ml)×100, or W/V%, of the pure barium sulfate contained in the barium suspension, totally excluding any additives. Examples for the range of density of the barium suspension of the present invention, the amount of water in milliliters to be added to make a suspension per 100 g of the barium powder preparation of the present invention, and the apparent viscosity ($\eta_{ap}$) are shown in Table 7.

TABLE 7

| Density (W/V %) | 260 | 270 | 280 | 290 |
|---|---|---|---|---|
| Water per 100 g powder (ml) | 15.8 | 14.4 | 13.0 | 11.8 |
| Apparent viscosity $\eta_{ap}$ (cp) | 72 | 94 | 150 | 250 |

Examples of the physical properties (rheological coefficients) of the extremely high density barium suspensions according to the present invention are shown in Table 8.

TABLE 8

| Barium density | 260 W/V % | 270 W/V % | 290 W/V % |
|---|---|---|---|
| Apparent viscosity (cp) | 70~95 | 80~110 | 250 |
| Yield value (dyne/cm$^2$) | 1.5~2.5 | 2.5~5.0 | 6.6 |
| Dynamic modulus G' (dyne/cm$^2$) | 5~12 | 14~30 | 19 |
| Dynamic loss G" (dyne/cm$^2$) | 1.0~4.0 | 2.5~6.0 | 6.2 |

The apparent viscosity was measured using a double rotating cylinder rheometer (Emila's rheometer) with a quadruple-speed rotor at a shear rate of 750 sec$^{-1}$. The yield value, G' and G" were measured using a cone-plate type rheometer (Shimadzu rheometer Model RM-1). The values of G' and G" are measurements at a plate moving frequency of 0.55 Hz. The cone radius was 4 cm, conic angle 4°, torsional constant 2.205×10$^6$ dyne·cm/rad, and conic tip-plate gap 175 μm.

A drop of the extremely high density barium suspension according to the present invention should cause no visible agglutination when added to a hydrochloric acid solution of pH 1.2 in a petri dish and agitated completely by horizontal circular motions of the petri dish (acid resistance test). No agglutination should be observed as checked in reference to distilled water placed in a petri dish, in which a drop of the sample is added and agitated in the same manner.

Test of Component Particles

After the component particles are produced, their apparent viscosity is measured and necessary physical property tests such as the acid resistance test are carried out.

A) Apparent viscosity

Measured under the conditions given above.

B) For the acid resistance test, hydrochloric acid solution of pH 1.2 is placed in a petri dish, and a 176±1 W/V% suspension (50 g of component particle powder suspended in 17 ml of distilled water) is prepared and a drop thereof added to the solution. The petri dish is immediately moved in quick horizontal circular motions to agitate the sample. The sample is checked for any agglutination of the particles. No agglutination is allowed for the sample to pass the acid resistance test. When this test is applied to commercial products, the only barium powder preparations that pass are Baritogen and Umbrasol A (tradenames, Fushimi Seiyakusho Co., Ltd.). Baritop P (Kaigen Corp.) showed substantial agglutination.

The acid resistance test is adapted from the method proposed by Shirakabe in 1970 in his work, "Gastric Double Contrast Method." In Shirakabe's method, pH varied 1.3 to 3.95, whereas it is 1.2 and no agglutination in reference to distilled water is allowed in the present invention, which comprise much stricter criteria.

Roller Theory and Viscosity Reduction Effect by the Mixture of Three Types Component Particles This theory, advocated for about 20 years by the inventor, claims that a mixture of large and small particles at an appropriate ratio of, say, 6:4 would significantly reduce the viscosity of the suspension. The word "roller" refers to a cylindrical support used to move a heavy load, which functions in a similar manner as the bearing balls in machinery.

Also, in order to precisely visualize the fine structures of the gastric mucosa (gastricae area) by the double contrast method, it was found in later studies that, rather than the simple mixture of large and small particles, the mixture of specific large, medium and small particles gives a better result. The ratio of the mixture should be adjusted strictly within a specific range in order to attain extremely high density barium suspension. The barium powder preparation of the present invention obtained by mixing such component particles and dispersing any secondary coagulating particles may be wrapped as necessary and, as in some of the commercial products, placed in a container designed for instant application.

Testing for Physical Properties Required for Ideal Contrast Medium

Finally, the barium powder preparation is tested lot by lot for the following items to check to see if it is suitable as an extremely high density barium suspension for upper gastrointestinal contrast examination, and is excluded if it is not:

a) Apparent viscosity measurement (measured by Emila's rheometer with a quadruple-speed rotor)
b) Acid resistance test
c) Static test: Yield value, etc., are measured by a cone-plate type rheometer to prepare a flow curve.
d) Dynamic test: Dynamic modulus (G') and dynamic loss (G") are measured by the same rheometer as above to prepare the frequency dependent curve of the viscoelasticity.
e) Bacteriological analysis (carried out according to the standards at Fushimi Seiyakusho Co. Ltd.)

Rheology of Barium Sulfate Suspension

When a cube sugar is put in water and stirred, it makes a clear solution, in which the molecules of sugar and water are mixed in a completely uniform phase. In such a solution, the viscosity is simple "pure viscosity." However, when insoluble matter such as a lump of clay is put in water and stirred, it makes a cloudy liquid. In such a liquid, particles that are visible under an optical microscope or, if not, much larger than the molecules of sugar, or so-called coarse particles, are suspended in water. The suspension is formed by two phases, i.e., the continuous phase of water and the discontinuous phase of the clay particles. Barium sulfate is insoluble to water as is clay and, thus, makes a water suspension of coarse particles. Ostwald called this system consisting of two phases a "dispersed system." Generally, in a dispersed system, the size and forms of the particles greatly affect the rheological properties of the system. The barium sulfate particles as observed under an electron microscope range in particle size from 0.1 μm to less than 100 μm, much bigger than the molecules of sugar and even slightly bigger than colloidal (macromolecular) particles. Thus, the suspension of barium sulfate is a type of dispersed system of coarse particles and presents various non-Newtonian phenomena which are characteristic of coarse particles.

Static Measurement of Rheology: Apparent Viscosity

Figure 4:
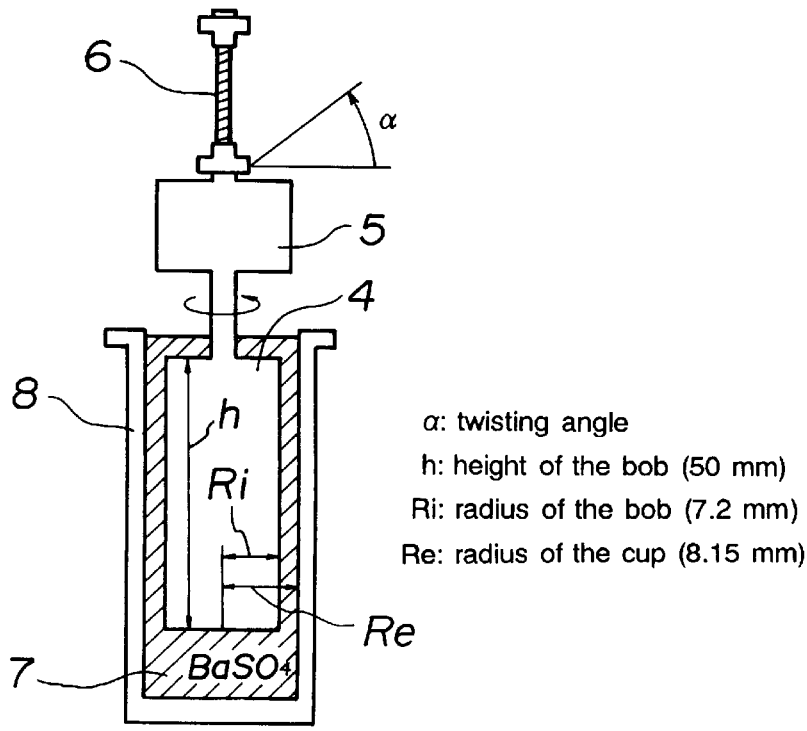
FIG. 4 is a cross-sectional view showing the section of an Emila's double rotating cylinder rheometer, and the formulas for calculating the shear rate and the shearing stress.

The rheological measurement of viscosity is the static measurement of the flow of a sample at a constant rate, i.e., constant flow. An Emila's double rotating cylinder rheometer 8 as shown in FIG. 4 is used. The bob 4 (a rotor integrated with a part comprising a motor 5 and suspended by a torsion wire 6) is rotated at a constant rate (Rate of shear, D), calculated by using the following formula;

$$D = \frac{4n \cdot \pi}{1-a} \quad (1)$$

(wherein $a=(Ri/Re)^2$, Re: radius of the cup (e.g., 8.15 mm), Ri: radius of the bob (e.g., 7.2 mm), n: number of circulations of the cup per second). The shearing stress (S) calculated by using the following formula (2);

$$S = \frac{\alpha \times W}{2Ri^2 h \cdot \pi} \quad (2)$$

(wherein α: twisting angle, W: wire constant, Ri: radius of the bob (e.g., 7.2 mm), h: height of the bob (e.g., 50 mm)), which acts on the bob 4 via sample 7 (dose of barium sample: 14 ml) is indicated on a dial (not shown) as the torsion angle a of the torsion wire 6. In a thixotropic sample, the indication keeps dropping for a while after rotation is started. The indication is read after about 10 seconds of rotation, when it has stabilized. The rheometer is equipped with nine different sizes of bobs. The indication is multiplied by 100 for the thinnest cylinder, and 1 for the thickest cylinder, to find the apparent viscosity ($\eta_{ap}$=S/D, in cp). It is a convenient direct-reading device. The test was carried out while maintaining the temperature constant at 24±1° C. by containing the cup 8 in a thermostatic chamber (not shown).

Flow Curve by Static Measurement

Figure 5A:
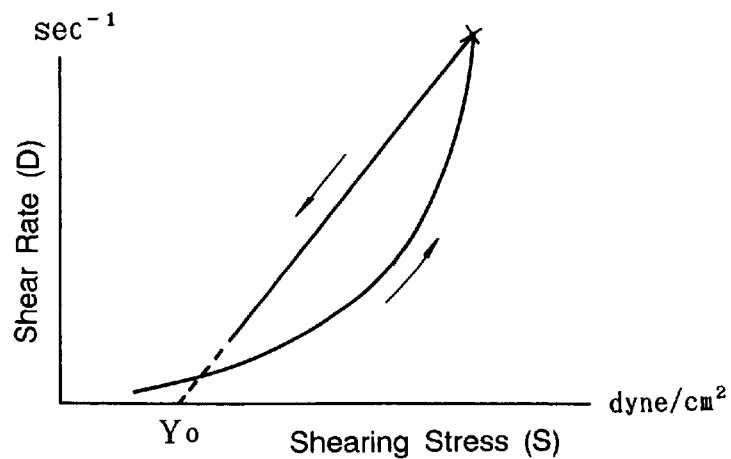
FIG. 5(A) is a hysteresis curve for a non-Newtonian flow and FIG. 5(B) is a diagram showing the relation between the shear rate and shearing stress of four kinds of non-Newtonian flow.

A fully equipped cone-plate type rheometer (Shimadzu rheometer Model RM-1) which can incrementally and decrementally change the shear rate in 10 steps was used. The shearing stress (dyne/cm$^2$) was measured while increasing and decreasing the shear rate (sec$^{-1}$). As shown in FIG. 5(A), the upward curve where the rotation speed increases and the downward curve where it decreases form a hysteresis loop. This is a flow curve. The extension of the downward curve, usually linear, intersects with the horizontal axis (stress axis) at the yield value (yield stress), $Y_0$, expressed in dyne/cm$^2$.

Flow Curve of Non-Newtonian Fluid

A high density suspension of coarse particles such as barium sulfate presents abnormal (structural) viscosity having a yield value. The upward portion of the flow curve of a non-Newtonian fluid is shown in FIG. 5(B).

Figure 5B:
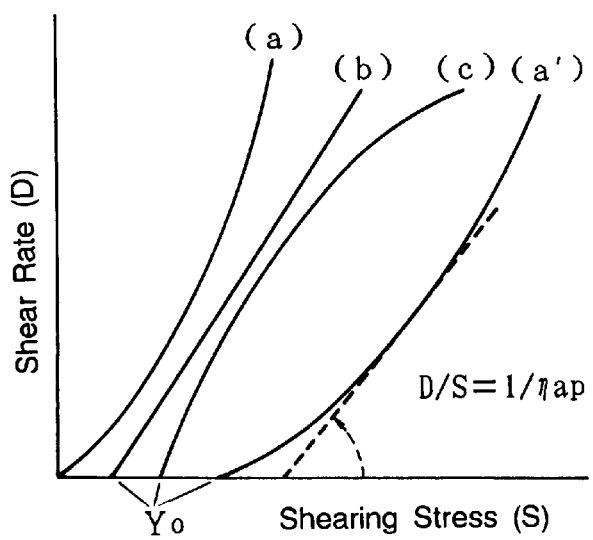

In FIG. 5(B), (a) shows an unusual non-Newtonian flow which does not have a yield value, and (a') shows a common non-Newtonian flow having a yield value, also called pseudoplastic flow. While the shear rate increases, the shearing stress does not increase substantially, indicating thixotropy, or a process of structural breakdown. Most high-quality barium usually falls in type (a'). Type (b) has a yield value but shows no thixotropy, in which the upward and downward curves overlap on a straight line, indicating plastic flow, which is often seen in plastic solids such as clay or macromolecular resins. However, when the yield value is very low and the upward and downward curves almost overlap on a straight line, the barium may have high fluidity and, thus, high quality. This type is closely approximated to a Newtonian flow. Type (c), in which the upward curve has a yield value and is upwardly convex, is an example of dilatancy. As the rotation speed of the rheometer increases, i.e., as the shear rate increases, the shearing stress continues to increase, a behavior contrary to thixotropy. Most barium suspensions exhibit dilatancy as the density Increases excessively, until the rheometer is finally stopped by the stress or broken by abnormal vibration.

At a density where dilatancy is observed, a barium suspension is not usable anymore. The most suitable static characteristic s as a contrast medium are a combination of minimal yield value and approximately Newtonian flow with slight thixotropy. The preferable apparent viscosity measured by an Emila's rheometer with quadruple-speed rotor is 50 to 300 cp, most preferably 70 to 100 cp. However, it needs not b e strictly lowered as the yield value, G' and G". At 50 cp or less, the suspendibility may suffer, making the suspension easily precipitable and inappropriate for serving. At 100 to 250 cp, if the yield value is low at 7 dyne/cm$^2$ or less, the suspension is still relatively easy to drink and acceptable. At 250 cp or above, the suspension is a little difficult to drink. A suspension at 300 cp or above is not suitable for application.

Frequency Dependent Curves by Dynamic Measurement

Figure 6:
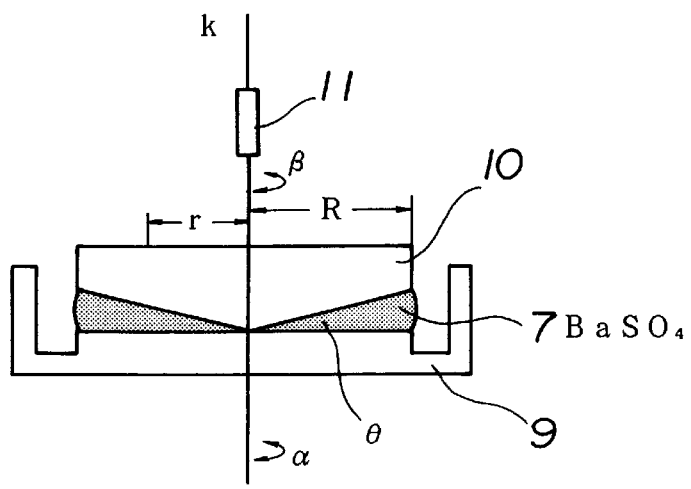
FIG. 6 is a cross-sectional view showing the section of a cone-plate type rheometer, and the formulas to calculate G', G" and $\eta$'.

FIG. 6 shows the cone-p late type rheometer (Shimadzu rheometer Model RM-1), in which the plate 9 is oscillated horizontally with a constant amplitude of a ($\alpha=\alpha_0\cos\omega t$) (rad), wherein $\alpha_0$: of oscillation of the plate, $\omega$: angular frequency (rad/sec), t: time) at five frequencies from 0.175 Hz to 0.9 Hz. The sample barium 7 induces oscillation of the same frequency and a different amplitude $\beta(\beta=\beta_0\cos(\omega t+\phi)$ (rad), wherein $\beta_0$: amplitude of oscillation of the cone, $\Omega$: angular frequency (rad/sec), t: time, $\phi$: phase difference between a and P (rad)) to the cone 10. A pen recorder (not shown) records the two sinusoidal oscillation outputs on the chart. The phase difference ($\phi$) and amplitude ratio (P=$\beta_0/\alpha_0$) of the fundamental frequency components (excluding the harmonics) of the two outputs were determined on the chart. Part 11 is a torsion wire. The values of $\phi$ and P are substituted into the two following formulae, (3) and (4), which are derived from the equations of motion of the cone as shown in the figure, to obtain the dynamic modulus (G') and the dynamic loss (G") at each of the five frequencies;

$$G' = \frac{-B(1 - \cos\phi/P)}{(1 - \cos\phi/P)^2 + (\sin\phi/P)^2} \quad (3)$$

$$G'' = \frac{B(1 - \sin\phi/P)}{(1 - \cos\phi/P)^2 + (\sin\phi/P)^2} \quad (4)$$

(wherein B=3k$\theta$/2$\pi$R$^3$, k: torsional constant of the wire (dyne-cm/rad), $\theta$: conic angle of the cone (rad)=4° (constant), R: radius of the cone (cm), $\phi$: phase difference between $\alpha$ and $\beta$ (rad)). Also, using the following formula (5);

$$\eta' = ''/\omega \quad (5)$$

the dynamic viscosity ($\eta'$, poise) was obtained. With the moving frequency (Hz) taken on the horizontal axis and G', G" and $\eta'$ (dyne/cm$^2$ and poise) on the vertical axis, the frequency dependent curves of the three coefficients were prepared.

The dynamic modulus (G') and the dynamic loss (G") are calculated, by using formulas that contain trigonometric functions but are fairly simple. They can be easily calculated using an electronic calculator by entering the formulas, then by putting in the measured values.

FIG. 7 shows examples of the frequency dependent curves of G', G" and $\eta'$ of an extremely high density barium suspension.

The value of $\eta'$ (poise) indicates the dynamic viscosity obtained by the above-mentioned formula (5).

To remove the harmonics, the sinusoidal output at the two lowest frequencies, 0.175 Hz and 0.375 Hz, were corrected for any minute distortion only by visual observation. In previous studies, a fast Fourier transform (FFT) analyzer (Ono Sokki Co.) was used for a very fine waveform analysis at a sampling rate of 2,000 Hz to remove harmonics and identify the natural component. However, very low frequency harmonics of about 1 Hz or less do not need extensive analysis of time constant. Also, the non-linearity of the sinusoidal wave may be caused presumably by the structural viscosity, i.e., non-Newtonian property, which is characteristic of the extremely high density barium. Therefore, only the waveforms that are undoubtedly classified as non-sinusoidal by visual observation were corrected using a French curve or other device on the chart while taking care not to change the amplitude. The values of dynamic modulus G' and dynamic loss G" were represented by measurements at 0.55 Hz.

Manifesting Way of Barium Density of Extremely High Density Barium Suspension

The barium density (W/V%) of the extremely high density barium suspension according to present invention was calculated by using the following equation:

$$W/V\% = a/(Va+Vb) \times 100\% = a/\{(0.222a+b)+c\} \times 100\%$$

(where, a: weight of pure barium sulfate (g), b: weight of additives (g), c: weight of water added (g), Va: volume of pure barium sulfate in the suspension, i.e., 0.222×a (ml) for a (g) of pure barium sulfate (specific gravity: 4.5), Vb: volume of additives in the suspension, with their specific gravity assumed as 1.0).

Extremely High Density Barium Suspension of the Present Invention can be Instantly Prepared In practical application at hospitals and other facilities, the barium powder preparation of the present invention, which may be supplied in plastic cups, will instantly make a 260 to 290 W/V% extremely high density suspension only by pouring a specified amount of tap water in it, sealing the container, and stirring intensely.

The extremely high density barium suspension of the present invention has a high suspension stability and, therefore, can be dispersed to uniformity only by stirring the container intensely as above even after it is stored in a refrigerator for a few days. For the last few years, an increasing number of high density barium products have been commercialized by domestic and foreign manufacturers, including ones that enable instant preparation. However, they have a common unreputable disadvantage of easily producing sludge on the bottom due to the instability of suspension, as well as excessive adhesion when used in double contrast examination. Also, stirring by furious shaking or ultrasonic agitation may have an adverse effect of increasing the viscosity, probably because the coagulating extremely small particles of 1 μm or less are dispersed excessively. Before application, therefore, they may be stirred well by horizontal motions, but not by furious cocktail-making style vertical motions unless they are to be used after 1 to 2 hours of interval, and not immediately.

Figure 8A:
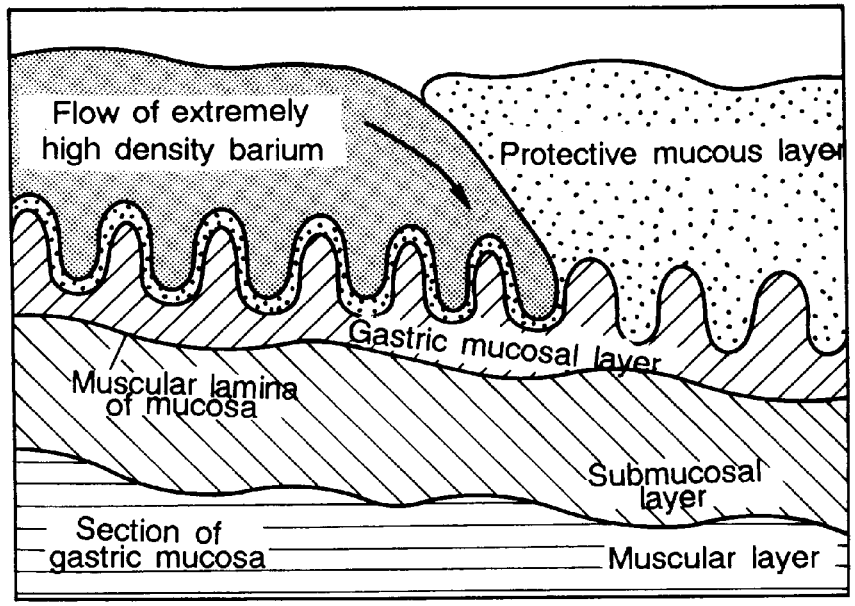
FIG. 8(A) is a schematic diagram showing how the extremely high density barium suspension according to the present invention sweeps the mucosal surface of the stomach.
Figure 8B:
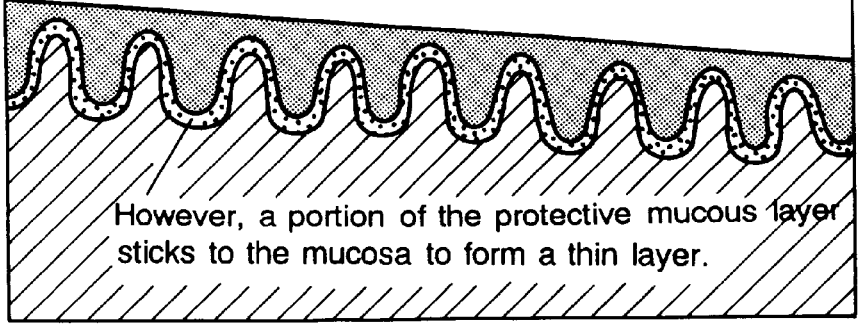
FIG. 8(B) is a schematic diagram showing how the extremely high density barium suspension according to the present invention adheres to the mucosal surface of the stomach after sweeping.

Principle of Double Contrast Radiography Using the Extremely High Density Barium Suspension of the Present Invention The extremely high density barium suspension of the present invention flows smoothly on the gastric mucosa while sweeping out the protective mucous layers covering it (sweeping flow) to form a thin layer, instead of adhering excessively, despite its extremely high density. As shown in FIGS. 8(A) and 8(B), a 260 W/V% or higher extremely high density barium suspension has a specific gravity almost twice as high as that of a 100 W/V% one. In consideration of the mechanics of rolling in double contrast examination, this difference in gravity is significant in removing the mucus. When barium of the conventional density is used, even a quick and rigorous washing flow by one rolling operation would be able to remove a only portion of the superficial mucus, thus requiring repeated rolling operations. On the contrary, the extremely high density barium suspension has a resultant vector directed more to the depth of the mucus and applies a "shoveling" force, thus removing the mucus more efficiently than simply deduced from the calculated gravity ratio.

Function of the Extremely High Density Barium Suspension of the Present Invention Is to Sweep the Gastric Mucosa The environment of the gastric mucosa is distinctive and severe, containing free acids and some mucus. The mucosal surface is covered with the protecting layers of mucus, and not easily accessible. In double contrast examination using the 140 W/V% Baritogen DX in the prior art mentioned earlier, a number of rigorous body rolling operations are required to wash out the mucous layers, as explained before, in addition to the use of a gastric tube to remove the free gastric mucus, for the best result.

In other words, the objective of rolling is to remove the protecting mucous layers that cover the entire gastric mucosa in order to achieve preferable barium adhesion. In the removal of the mucus, two mechanical parameters are important, i.e., the specific gravity of the barium suspension, or gravitational potential, and the acceleration torque of the barium that moves over the gastric mucosa by rolling.

In Mackintosh's experiment with a porcine stomach, barium adhesion preferable for the visualization of the gastricae area is, as shown in FIG. 8(B), a state where it adheres thinly to the mucosal surface after the mucous layers have been removed. This experiment is significant in understanding the principle of double contrast radiography.

Based on this supposition, the inventor performed a mechanical analysis of the principle of double contrast examination, focusing on the correlation between the rolling speed and barium density in clinical application. Considering that the specific gravity of barium suspension increases with its barium density, as can be seen in Table 9, which shows specific gravity by density, the following argument is educed.

FIG. 9 is a schematic diagram showing the mechanics of rolling in the double contrast examination of the stomach.

TABLE 9

Specific gravity of barium suspension by density

| Product | Density (W/V %) | Specific gravity (g/ml) |
|---|---|---|
| Baritogen Sol (example of ordinary density barium) | 100 | 1.78 |
| Super-high density barium | 250 | 2.96 |
| Extremely high density barium | 260 | 3.02 |
|  | 270 | 3.11 |
|  | 280 | 3.18 |
|  | 290 | 3.26 |

Figure 9A:
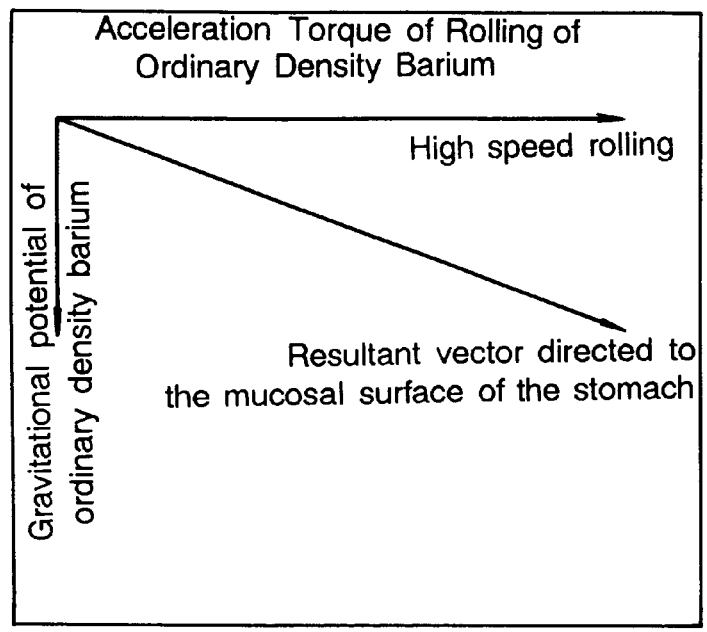
FIG. 9(A) is a schematic diagram showing the mechanics of rolling in the double contrast examination of the stomach for a barium suspension of conventional density and FIG. 9(B) is a schematic diagram showing the mechanics of rolling in the double contrast examination of the stomach for the extremely high density barium suspension according to the present invention.
Figure 9B:
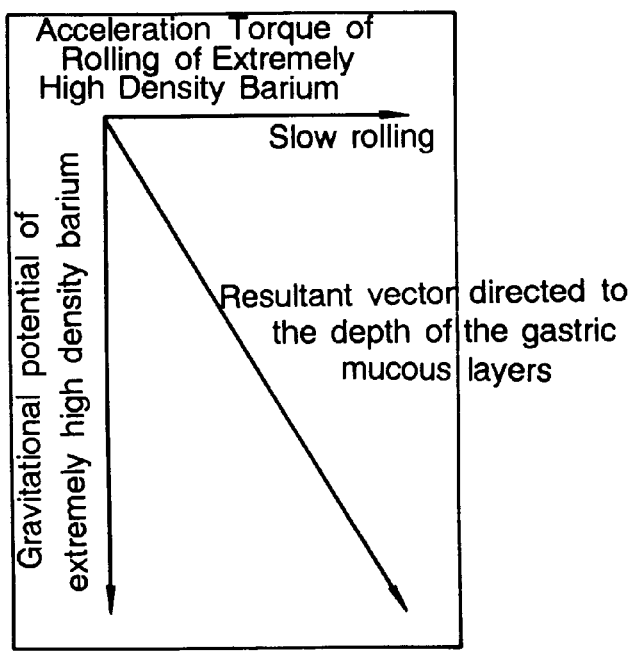

The gravitational potential of barium is determined by the specific gravity of the barium suspension. If the specific gravity doubles, so does the potential. A 280 W/V% barium suspension has an approximately twice as high specific gravity as the aforementioned 100 W/V% Baritogen Sol. Therefore, as shown in FIG. 9(A), the resultant vector of the former to the gastric mucosa is relatively flat and far from an angle effective for the removal of the mucus, even at a rolling speed that is two to three times that for the latter. By contrast, as shown in FIG. 9(B), the former can apply a comparable shearing force toward the depth of the mucous layers at an angle more effective for the removal of the mucus, at a rolling speed that is ½ to ⅓ of that of the latter. This hypothesis is proved by the fact that, in the latest contrast examinations using extremely high density barium of 260 W/V% and no gastric tube, only one cycle of extremely slow posture change at 2 seconds per half a cycle (angular velocity: 45°/sec) from the dorsal supine position to the right lateral side position, then return to the dorsal supine position, has been found enough to visualize the Class A gastricae area by almost 100%.

The function of the extremely high density barium in the double contrast examination of the stomach is, in addition to enhancing the contrast, to sweep the mucosal surface of the stomach slowly. This is a totally new idea no one has ever come up with. However, it is necessary that, after barium sweeps away the mucus, most of it flows away swiftly, with the remaining portion covering the mucosa thinly as shown in FIG. 8(B) quoted earlier, for the sweeping function to be maintained. Thus, it is imperative that the four coefficients, i.e., apparent viscosity ($\eta_{ap}$), yield value ($Y_0$), dynamic modulus (G'), and dynamic loss G", are low enough as stipulated before to make the suspension specially smooth, "Kire" in Japanese expression, while it is resistant to acid.

Rolling May Be Extremely Slow for Extremely High Density Barium

There is no literature with clear instruction on the body rolling speed. As rolling speed is the speed of circular motions, the most scientific and practically convenient expression would be an angular velocity, i.e., degrees per second, as shown in Table 10.

TABLE 10

| Barium density | Angular velocity of rolling | Time per 90° rotation | Name and type of product available |
|---|---|---|---|
| 100 W/V % | 270°/sec | 0.3 sec or less | Sol agent: Baritogen Sol 100, etc.*1 |
| 140 W/V % | 180°/sec | 0.5 sec | Ordinary density powder agent: Baritogen DX*2 |
| 174 W/V % | 90°/sec | 1.0 sec | High density powder agent: Baritogen*3 |
| 260 W/V % | 45°/sec | 2.0 sec or more | Extremely high density: 250 to 290 W/V % trial product |

*1–*3Tradename, Fushimi Seiyakusho Co., Ltd.

A body rolling rate of 0.5 seconds or less per 90° is speedy "washing" rolling, while 1.0 second or more is slow rolling. There is no literature describing the rolling speed this objectively. At an extremely high density of 260 W/V% or above, the rolling speed may be extremely slow at 2 seconds or more per 90° (half a cycle).

The double contrast examination of the stomach depends largely on the individual skill of the operator. In other words, the most skilled should be able to point out what is wrong with the inexperienced operator. However, this is practically not as easy as it seems, and more so if the required operation is more delicate and fine, due to the complexity of the conditions such as the complicated environment of the gastric mucosa, difference in barium density, visco-elasticity of individual contrast medium, and rolling method.

As mentioned earlier, the lately commercialized high-density agents with rated barium densities of 200 W/V% or over have a common disadvantage of easily precipitating and forming sludge. This overly high visco-elasticity hampers spreading of the medium and makes it a too thick layer and, therefore, visualizes only the gastric folds but not the area gastricae.

On the other hand, if the density is too low, the resultant vector is flatter as shown in FIG. 9(A), the barium only flows over the protective mucous layers without removing much of them, requiring a number of posture changes for the removal of the mucus.

On-the-Fly Double Contrast Examination for Efficient Visualization of Area Gastricae The extremely high density barium with a high specific gravity mechanically sweeps the mucosa and, therefore, only requires one cycle of rolling with the patient's body on the table, to visualize the fine mucosal structures such as the area gastricae on a double contrast picture. In other words, it enables tubeless and on-the-fly double contrast examination, unlike the barium of the conventional density which requires repeated high-speed rigorous rolling to wash the mucosal surface of the stomach. In the extremely high density barium, intense posture changes for "washing" would only result in the barium being spattered and bring about an adverse effect against its uniform adhesion to the gastric wall.

For the performance judgment of barium in clinical application, the visualization of the area gastricae in double contrast radiography is used as in index. When the extremely high density barium according to the present invention is used in clinical examination, only one very slow rolling operation is enough to visualize the area gastricae.

Figure 10:
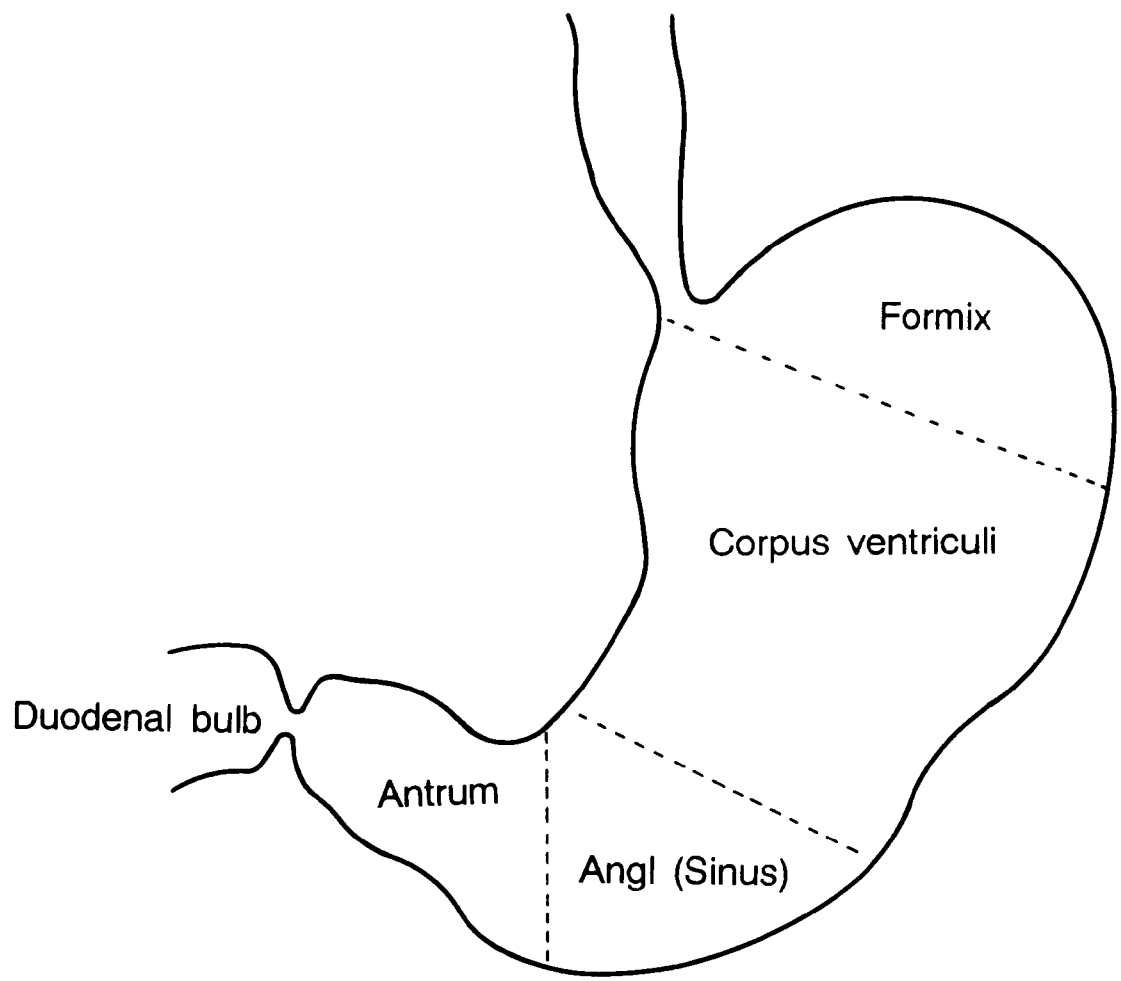
FIG. 10 is a diagram showing the regions on the inside mucosal membrane of the stomach.

According to the criteria for evaluating barium on an X-ray picture as shown in Table 11, the 260 W/V% extremely high density barium was evaluated for visualization in the double contrast picture of the posterior wall of the stomach. Class A, in which visualization is positive, is subdivided into A, Ab and AB. In this class, gastricae area is observed in the entire antral region illustrated in FIG. 10 or in its comparable or wider region of the gastric mucosa. The area visualization is the percentage of the number of tests. The result is shown in Table 12. When the 260 W/V% extremely high density barium was used in 27 routine examinations, it effectively visualized the gastricae area, with Class A accounting for 25 cases, or 93%.

Figure 11:
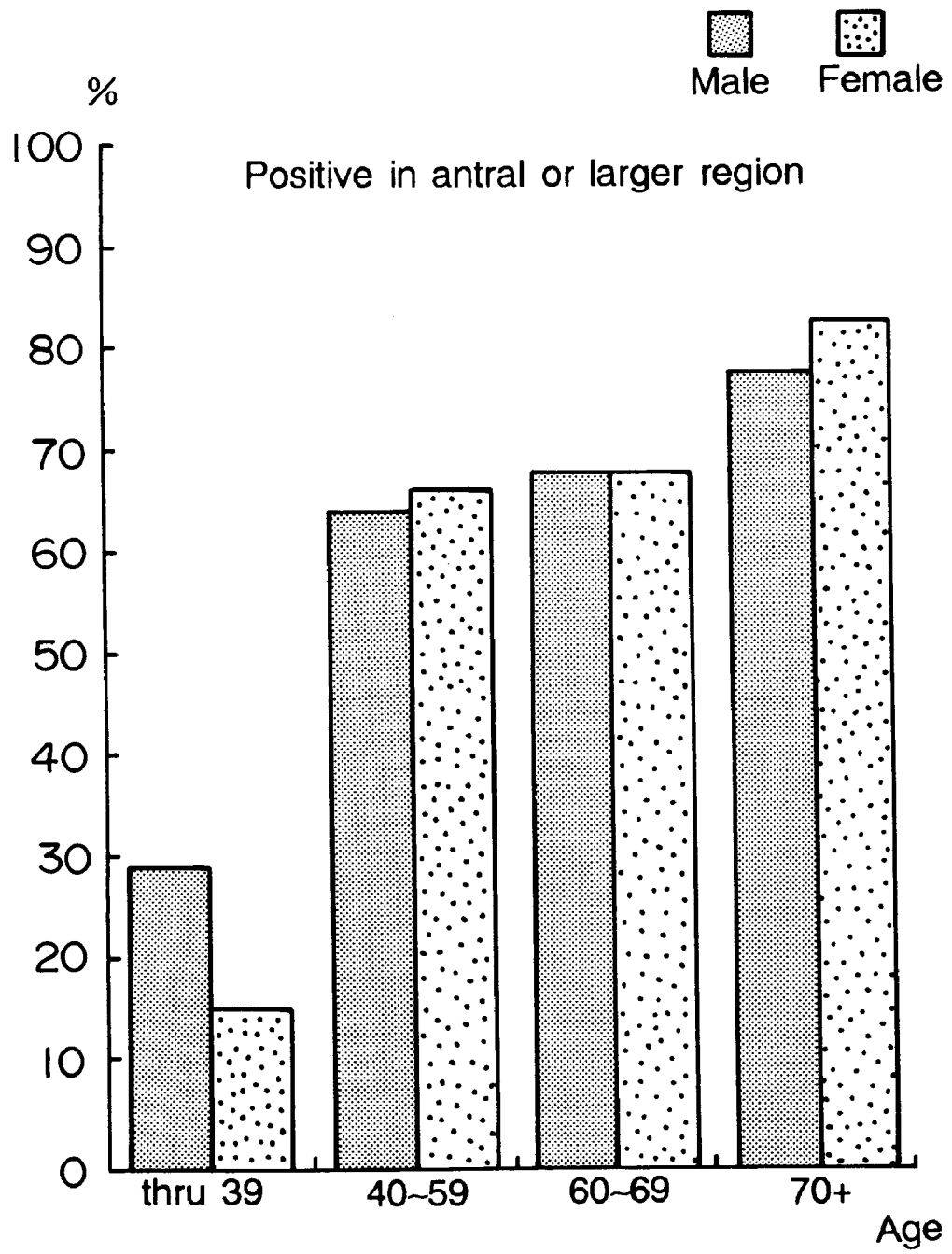
FIG. 11 is a bar chart showing the visualization of the gastricae area by age and sex for the extremely high density barium suspension according to the present invention.

Also, in the 456 cases where the 260 W/V% extremely high density barium was used, the gastricae area were visualized more efficiently in older patients, as shown in FIG. 11. These results clearly confirm the clinical applicability of the extremely high density barium.

TABLE 11

Criteria for Evaluating Barium on an X-Ray Picture

| Class A | A | Area gastricae visualized in entire gastric mucosa. |
|---|---|---|
| | Ab | Entire antral region and other regions, corpus ventriculi, etc. |
| | AB | Entire antral region or its comparable area. |
| Class B | BA | Part of the mucosa smaller than entire antral region. |
| | B | No area gastricae observed in any region. |

TABLE 12

Result of Visualization of Gastricae Area

| | | | Class A | | | Class B | |
|---|---|---|---|---|---|---|---|
| Test No. | Sex | Age | A | Ab | AB | BA | B |
| 142 | ♀ | 71 | | | + | | |
| 422 | ♂ | 48 | | | + | | |
| 426 | ♀ | 88 | | | + | | |
| 451 | ♀ | 82 | | | + | | |
| 445 | ♂ | 41 | | | | + | |
| 323 | ♀ | 54 | | | + | | |
| 442 | ♂ | 58 | | | + | | |
| 440 | ♂ | 81 | | | + | | |
| 489 | ♀ | 80 | | + | | | |
| 484 | ♀ | 47 | | + | | | |
| 471 | ♀ | 72 | | + | | | |
| 473 | ♂ | 60 | | + | | | |
| 483 | ♂ | 50 | | | + | | |
| 478 | ♂ | 77 | | + | | | |
| 476 | ♀ | 78 | + | | | | |
| 483 | ♂ | 86 | | | + | | |
| 472 | ♀ | 48 | + | | | | |
| 475 | ♀ | 79 | | + | | | |
| 486 | ♀ | 54 | + | | | | |
| 432 | ♀ | 67 | | | + | | |
| 474 | ♀ | 84 | | | + | | |
| 505 | ♂ | 65 | | + | | | |
| 506 | ♀ | 55 | | + | | | |
| 502 | ♂ | 57 | | | | + | |
| 507 | ♂ | 54 | | + | | | |
| 508 | ♀ | 61 | | + | | | |
| 504 | ♀ | 72 | | | + | | |
| Total: 27 cases | | | 3 | 10 | 12 | 2 | |

*Class A: 93%

Examination without Using Gastric Tube and Parasympathicolytics

The upper gastrointestinal examination using the extremely high density barium of the present invention normally does not require the use of a gastric tube nor the injection of parasympathicolytics that suppresses the mucous secretion and gastric peristalsis. In the pretreatment for the removal of the gastric juice, the patient breathes deeply and repeatedly in a right lateral side position to contract the abdominal muscles to squeeze out the gastric juice through the pylorus to the duodenum (pumping).

Recently, an increasing number of X-ray examinations of the stomach are handled only by radiological technicians, such as in the gastrointestinal mass survey, which amount to over six million per year, and at the overloaded university or public hospital, cancer center, and other medical facilities. In these cases, absolutely no gastric tube or parasympathicolytics should be used since a technician is officially prohibited from contacting a patient and injecting. Recently, also, the proportion of elderly subjects has been increasing significantly in most medical services, calling for the urgent improvement of examination procedures in order to relieve the physical and mental stress on the patients. The tubeless, non-parasympathicolytics and on-the-fly double contrast method meets these requirements.

In the upper gastrointestinal X-ray examination according to the present invention using the extremely high density barium according to the present invention, a procedure for washing the mucosal surface by repeated, furious and quick rolling as required for barium in the prior art is unnecessary; only one slow rolling operation with a patient on the table is enough to easily visualize fine mucosal structures, including area gastricae, on the double contrast pictures.

In general, the use of a gastric tube is unnecessary. Double contrast radiography can be carried out on-the-fly without the injection of a parasympatholytic agent for suppressing mucous secretion and peristalsis.

Also, high contrast is achieved while fuzziness is minimized by an advantage of high voltage radiography. The gastric mucosa can be washed by rolling at a low speed. Only a small amount of contrast medium is required, serving for comfort and reducing side effects such as constipation. The examination procedure is made easier, and then relieves the physical stress on the patient, which makes the X-ray gastric examination useful for application to old, grave or handicapped patients, who have difficulty in changing postures. Furthermore, the discovery of early gastric cancers and the upper gastrointestinal diagnosis of gastric ulcer and other diseases are effectively enabled, implying tremendous clinical applicability and medical industry.

What is claimed is:

1. A barium powder preparation consisting of large, medium and small component particles of pure barium sulfate coated with a composite additive consisting of Gum Tragacanth and Carrageenan, said large, medium and small component particles being mixed at a weight ratio of [large component particles]:[medium component particles]:[small component particles]=2:1:1, the particle size distribution of said original pure barium sulfate particles being normal distribution as measured by a Coulter Counter, having peaks at 8 µm for the large particles, 2.0 to 2.5 µm for the medium particles and 0.8 to 1 µm for the small particles, the ratio of the contents of Gum Tragacanth and Carrageenan in said composite additive to said pure barium sulfate particles being 1:10 for said large particles, 1:9±1 for said medium particles, and 1:0.9±0.1 for said small particles, and the ratio of the effective Gum Tragacanth contents in said large, medium and small particles is identical to the ratio of the specific surface areas of said large, medium and small particles, wherein said specific surface areas are determined according to said measurement of particle size distribution, and said effective Gum Tragacanth contents are calculated using the following formula Effective Gum Tragacanth content=[Gum Tragacanth content]+[Carrageenan content]×$\frac{1}{2.5}$, (wherein the contents is expressed in weight percent, and the viscosity reduction effect of Gum Tragacanth is assumed as 2.5 times that of Carrageenan).

2. An extremely high density barium suspension for upper gastrointestinal contrast examination with a pure barium sulfate density of 260 to 290 W/V% comprising a suspension of the barium powder preparation according to claim 1 in water, having an apparent viscosity ($\eta_{ap}$) of 70 to 250 cp, a yield value ($Y_0$) of 1.5 to 6.6 dyne/cm$^2$, a dynamic modulus (G') of 5 to 19 dyne/cm$^2$, and a dynamic loss (G") of 1 to 6.2 dyne/cm$^2$, the lower and upper values expressing the minimums and maximums of respective coefficients by density variation, where the apparent viscosity is measured by a double rotating cylinder rheometer (Emila's rheometer) with a quadruple-speed rotor and other coefficients by a cone-plate type rheometer, and G' and G" are measured at a rheometer plate moving frequency of 0.55 Hz.

3. A process for producing the barium powder preparation according to claim 1, comprising the steps of:

preparing the large, medium and small component particles according to a specified procedure of (A) through (C) below, (A) a procedure of (1) through (4) below for producing the large component particles comprising:

(1) a step for mixing a composite additive, wherein the ratio of the Gum Tragacanth content and Carrageenan content in the large particles of pure barium sulfate is 1:10, and the effective Gum Tragacanth content achieves the maximum viscosity reduction effect of the large particles;

(2) a step for allowing said composite additive consisting of Gum Tragacanth and Carrageenan to swell by adding distilled water accounting for 80±5% of the total water amount necessary for the kneading process in (3) below (13.5±1 wt % of the original large particles) to said composite additive, and conditioning for 24 to 30 hours at room temperature;

(3) a step for transferring the large particles of pure barium sulfate, the swollen composite additive, and distilled water making up for the remaining portion of said total water amount, in this order, into a kneader, and kneading for 90±5 minutes, while controlling the temperature so that, if kneading is started at 25±5° C., the kneading gradually increases the mechanical load of the kneader and causes liquidization at the peak thereof, and, if the kneading is continued adequately after the liquidization, the temperature increases gradually to 33±2° C. and remains as is or decreases slightly; and (4) a step for adding distilled water to the pasty large component particles obtained by the kneading, to make a 100±10 W/V% aqueous suspension, and heating to dry and sterilize by a drum dryer, to obtain the large component particles as powder, (B) a procedure of (1) through (4) below for producing the medium component particles, comprising:

(1) a step for mixing a composite additive, wherein the ratio of the Gum Tragacanth content and Carrageenan content in the medium particles of pure barium sulfate is 1:9±1, and the ratio of the effective Gum Tragacanth content in the large particles, as specified in the method for producing the large component particles, and the effective Gum Tragacanth content in the medium particles is identical to the ratio of the specific surface areas of the large and medium particles;

(2) a step for allowing said composite additive consisting of Gum Tragacanth and Carrageenan to swell by adding distilled water accounting for 80±5% of the total water amount necessary for the kneading process in (3) below (15±1 wt % of the original medium particles) to said composite additive, and conditioning for 24 to 30 hours at room temperature;

(3) a step for transferring the medium particles of pure barium sulfate, the swollen composite additive, and distilled water making up for the remaining portion of said total water amount, in this order, into a kneader, and kneading for 60±5 minutes, while controlling the temperature so that, if kneading is started at 25±5° C., the kneading gradually increases the mechanical load of the kneader and causes liquidization at the peak thereof, and, if the kneading is continued adequately after the liquidization, the temperature increases gradually to 37±2° C. and remains as is or decreases slightly; and (4) a step for adding distilled water to the pasty medium component particles obtained by the kneading, to make a 100±10 W/V% aqueous suspension, and heating to dry and sterilize by a drum dryer, to obtain the medium component particles as powder, (C) a procedure of (1) through (4) below for producing the small component particles, comprising:

(1) a step for mixing a composite additive, wherein the ratio of the Gum Tragacanth content and Carrageenan content in the small particles of pure barium sulfate is 1:0.9±0.1, and the ratio of the effective Gum Tragacanth content in the large particles, as specified in the method for producing the large component particles, and the effective Gum Tragacanth content in the small particles is identical to the ratio of the specific surface areas of the large and small particles;

(2) a step for allowing said composite additive consisting of Gum Tragacanth and Carrageenan to swell by adding distilled water accounting for 80±5% of the total water amount necessary for the kneading process in (3) below (15±1 wt % of the original small particles) to said composite additive, and conditioning for 24 to 30 hours at room temperature;

(3) a step for transferring the small particles of pure barium sulfate, the swollen composite additive, and distilled water making up for the remaining portion of said total water amount, in this order, into a kneader, and kneading for 90±5 minutes, while controlling the temperature so that, if kneading is started at 25±5° C., the kneading gradually increases the mechanical load of the kneader and causes liquidization at the peak thereof, and, if the kneading is continued adequately after the liquidization, the temperature increases gradually to 40±2° C. and remains as is or decreases slightly; and (4) a step for adding distilled water to the pasty small component particles obtained by the kneading, to make a 100±10 W/V% aqueous suspension, and heating to dry and sterilize by a drum dryer, to obtain the small component particles as powder, mixing said three kinds of powders (A)-(C) completely at a weight ratio of [large component particles]:[medium component particles]:[small component particles]= 2:1:1, crushing the mixture to disperse any secondary resulting coagulation of particles, and wrapping it as necessary.

4. A process for producing the extremely high density barium suspension for upper gastrointestinal examination, wherein the barium powder preparation according to claim 1 is mixed with and suspended in water.

5. A method of X-ray upper gastrointestinal examination, wherein the extremely high density barium suspension according to claim 2 is used as a contrast medium for upper gastrointestinal double contrast examination.

6. A method of X-ray upper gastrointestinal examination according to claim 5 in which no gastric tube or any parasympathicolytics are employed.

* * * * *